United States Patent
Mendels et al.

(10) Patent No.: US 9,074,920 B2
(45) Date of Patent: Jul. 7, 2015

(54) APPARATUS AND METHOD FOR BEDSIDE COLLECTION OF BODY FLUIDS AND AUTOMATIC VOLUME LEVEL MONITORING

(75) Inventors: Yair Mendels, Moza Elit (IL); Ilya Revzin, Jerusalem (IL); Vered Manny-Aframian, Jerusalem (IL); Eldad Gabriel Rubinstein, Jerusalem (IL)

(73) Assignee: Biometrix Ltd., Jerusalem (IL)

( * ) Notice: Subject to any disclaimer, the term of this patent is extended or adjusted under 35 U.S.C. 154(b) by 630 days.

(21) Appl. No.: 13/375,693

(22) PCT Filed: Jun. 1, 2010

(86) PCT No.: PCT/US2010/036887
§ 371 (c)(1), (2), (4) Date: Dec. 1, 2011

(87) PCT Pub. No.: WO2010/141458
PCT Pub. Date: Dec. 9, 2010

(65) Prior Publication Data
US 2012/0078137 A1    Mar. 29, 2012

Related U.S. Application Data

(60) Provisional application No. 61/183,835, filed on Jun. 3, 2009.

(51) Int. Cl.
*A61B 5/00* (2006.01)
*B65D 81/00* (2006.01)
(Continued)

(52) U.S. Cl.
CPC ............ *G01F 23/18* (2013.01); *A61B 10/007* (2013.01); *A61B 5/14865* (2013.01); *A61B 5/153* (2013.01);
(Continued)

(58) Field of Classification Search
CPC ........................................................ A61B 5/00
USPC ......... 600/573, 574, 575, 576, 579, 580, 581, 600/582, 584
See application file for complete search history.

(56) References Cited

U.S. PATENT DOCUMENTS 3,894,845 A * 7/1975 McDonald ................... 422/430
3,957,082 A   5/1976 Larson et al.
(Continued)

FOREIGN PATENT DOCUMENTS

DE   3544676      7/1986
DE   3544676 A1   7/1986
(Continued)

OTHER PUBLICATIONS

International Preliminary Report of Patentability dated Dec. 6, 2011 for PCT/US10/37043 filed Jun. 2, 2010.
(Continued)

*Primary Examiner* — Rene Towa
*Assistant Examiner* — May Abouelela
(74) *Attorney, Agent, or Firm* — Fleit Gibbons Gutman Bongini & Bianco PL; Martin Fleit; Paul D. Bianco

(57) ABSTRACT

A bedside apparatus and method designed to collect and monitor liquids output from a catheterized patient including an electronic unit and one of a plurality of defined disposable collecting and measuring rigid vessels that may differ in shape and size. Each defined vessel has at least one inlet to connect to a catheter outputting liquid from a patient in order to collect the liquid in the defined vessel. The defined vessel has at least one outlet valve to control draining of liquid from the vessel. An electronic unit has a configuration to receive the defined vessel and to securely mount and hold the defined vessel in a fixed relationship. The electronic unit further has a liquid level sensing device located in juxtaposition to the defined vessel to sense the level of liquid contained in the vessel.

24 Claims, 21 Drawing Sheets

(51) Int. Cl.

| | | |
|---|---|---|
| *B65D 33/00* | (2006.01) | |
| *A61D 5/00* | (2006.01) | |
| *A61F 2/02* | (2006.01) | |
| *G01F 23/18* | (2006.01) | |
| *A61B 5/20* | (2006.01) | |
| *G01F 23/00* | (2006.01) | |
| *G01F 23/292* | (2006.01) | |
| *A61B 10/00* | (2006.01) | |
| *A61B 5/1486* | (2006.01) | |
| *A61B 5/153* | (2006.01) | |
| *A61B 5/155* | (2006.01) | |
| *A61B 5/157* | (2006.01) | |

(52) U.S. Cl.
CPC ............... *A61B 5/155* (2013.01); *A61B 5/157* (2013.01); *A61B 5/205* (2013.01); *A61B 5/208* (2013.01); *G01F 23/0069* (2013.01); *G01F 23/0076* (2013.01); *G01F 23/0092* (2013.01); *G01F 23/2921* (2013.01); *G01F 23/2924* (2013.01); *G01F 23/2927* (2013.01)

(56) References Cited

U.S. PATENT DOCUMENTS

| | | | |
|---|---|---|---|
| 4,177,835 A | | 12/1979 | Paley |
| 4,257,416 A | | 3/1981 | Prager |
| 4,286,464 A | * | 9/1981 | Tauber et al. ............... 73/293 |
| 4,343,316 A | * | 8/1982 | Jespersen ............... 600/584 |
| 4,343,516 A | | 8/1982 | Aden |
| 4,432,392 A | | 2/1984 | Paley |
| 4,448,205 A | | 5/1984 | Stenkvist |
| 4,532,936 A | * | 8/1985 | LeVeen et al. ............... 600/575 |
| 4,631,061 A | * | 12/1986 | Martin ............... 604/318 |
| 4,658,655 A | * | 4/1987 | Kanno ............... 73/863.85 |
| 4,658,834 A | * | 4/1987 | Blankenship et al. ........ 600/584 |
| 4,745,929 A | | 5/1988 | Silver |
| 4,773,430 A | * | 9/1988 | Porath ............... 600/581 |
| 4,838,855 A | | 6/1989 | Lynn |
| 5,190,525 A | | 3/1993 | Oswald |
| 5,192,269 A | | 3/1993 | Poli et al. |
| 5,207,645 A | | 5/1993 | Ross et al. |
| 5,217,432 A | | 6/1993 | Rudzena et al. |
| 5,250,040 A | | 10/1993 | Parks et al. |
| 5,265,621 A | | 11/1993 | Simpson et al. |
| 5,324,266 A | | 6/1994 | Ambrisco et al. |
| 5,374,248 A | | 12/1994 | Lopez |
| 5,374,401 A | * | 12/1994 | von Berg ............... 422/534 |
| 5,403,279 A | * | 4/1995 | Inaba et al. ............... 604/65 |
| 5,431,185 A | | 7/1995 | Shannon et al. |
| 5,486,159 A | | 1/1996 | Mahurkar |
| 5,527,299 A | | 6/1996 | Cude |
| 5,629,498 A | * | 5/1997 | Pollock et al. ............... 177/15 |
| 5,699,821 A | | 12/1997 | Paradis |
| 5,738,662 A | | 4/1998 | Shannon et al. |
| 5,747,824 A | * | 5/1998 | Jung et al. ............... 250/577 |
| 5,758,643 A | | 6/1998 | Wong et al. |
| 5,769,087 A | * | 6/1998 | Westphal et al. ............ 600/573 |
| 5,776,077 A | | 7/1998 | Kottig |
| 5,820,601 A | | 10/1998 | Mayer |
| 5,891,051 A | * | 4/1999 | Han et al. ............... 600/573 |
| 5,961,472 A | | 10/1999 | Swendson et al. |
| 6,036,654 A | | 3/2000 | Siman et al. |
| 6,113,554 A | * | 9/2000 | Gilcher et al. ............... 600/573 |
| 6,159,164 A | | 12/2000 | Neese et al. |
| 6,206,851 B1 | | 3/2001 | Prosel |
| 6,364,861 B1 | | 4/2002 | Feith et al. |
| 6,402,702 B1 | * | 6/2002 | Gilcher et al. ............... 600/573 |
| 6,406,458 B1 | | 6/2002 | Tillander |
| 6,428,520 B1 | | 8/2002 | Lopez et al. |
| 6,582,379 B1 | * | 6/2003 | Stisen ............... 600/573 |
| 6,592,544 B1 | | 7/2003 | Currier et al. |
| 6,640,649 B1 | * | 11/2003 | Paz et al. ............... 73/861.41 |
| 7,112,177 B2 | | 9/2006 | Christensen et al. |
| 7,396,348 B2 | | 7/2008 | Newton et al. |
| 7,563,243 B2 | | 7/2009 | Mendels |
| 7,608,042 B2 | | 10/2009 | Goldberger et al. |
| 7,618,412 B2 | | 11/2009 | Chernack |
| 7,680,042 B2 | | 3/2010 | Rambo et al. |
| 7,722,584 B2 | * | 5/2010 | Tanaka et al. ............... 604/317 |
| 7,931,630 B2 | * | 4/2011 | Nishtala et al. ............... 604/318 |
| 8,034,021 B2 | | 10/2011 | Mendels |
| 8,471,231 B2 | * | 6/2013 | Paz ............... 250/573 |
| 8,523,797 B2 | * | 9/2013 | Lowery et al. ............... 604/4.01 |
| 2001/0004285 A1 | | 6/2001 | Cadell et al. ............... 356/39 |
| 2002/0161314 A1 | * | 10/2002 | Sarajarvi ............... 600/573 |
| 2003/0135165 A1 | | 7/2003 | Chernack |
| 2004/0176703 A1 | | 9/2004 | Christensen et al. |
| 2005/0096627 A1 | * | 5/2005 | Howard ............... 604/500 |
| 2005/0121103 A1 | | 6/2005 | Steigerwalt et al. |
| 2005/0247121 A1 | * | 11/2005 | Pelster ............... 73/223 |
| 2005/0267445 A1 | | 12/2005 | Mendels |
| 2006/0058702 A1 | * | 3/2006 | Christensen et al. ........ 600/561 |
| 2006/0194325 A1 | * | 8/2006 | Gable et al. ............... 436/45 |
| 2006/0270971 A1 | * | 11/2006 | Gelfand et al. ............... 604/66 |
| 2007/0060872 A1 | * | 3/2007 | Hall et al. ............... 604/66 |
| 2007/0179436 A1 | * | 8/2007 | Braig et al. ............... 604/66 |
| 2007/0255167 A1 | * | 11/2007 | Christensen et al. ........ 600/561 |
| 2008/0033400 A1 | | 2/2008 | Holper et al. ............... 604/541 |
| 2009/0281460 A1 | * | 11/2009 | Lowery et al. ............... 600/584 |
| 2009/0287170 A1 | * | 11/2009 | Otto ............... 604/318 |
| 2009/0314101 A1 | * | 12/2009 | Levine ............... 73/861.08 |
| 2010/0022967 A1 | | 1/2010 | Mendels |
| 2010/0137778 A1 | | 6/2010 | Kunjan et al. |
| 2010/0211032 A1 | * | 8/2010 | Tsai et al. ............... 604/319 |
| 2010/0217154 A1 | | 8/2010 | Deshmukh et al. |
| 2011/0009720 A1 | * | 1/2011 | Kunjan et al. ............... 600/316 |
| 2011/0288494 A1 | | 11/2011 | Mendels |

FOREIGN PATENT DOCUMENTS

| | | |
|---|---|---|
| EP | 0242128 | 10/1987 |
| EP | 0242128 A1 | 10/1987 |
| EP | 0901778 | 7/1998 |
| EP | 0901778 A2 | 3/1999 |
| EP | 1749549 | 8/2005 |
| EP | 1749549 A1 | 2/2007 |
| FR | 2358601 | 2/1978 |
| FR | 2513520 | 4/1983 |
| WO | 00/27452 | 5/2000 |
| WO | 2004/045704 | 3/2004 |
| WO | 2004-045704 | 6/2004 |
| WO | 2010141458 | 12/2010 |
| WO | 2010141563 | 12/2010 |

OTHER PUBLICATIONS

International Preliminary Report of Patentability dated Dec. 6, 2011 for PCT/US10/36887 filed Jun. 1, 2010.

International Search Report published Dec. 23, 2004 for PCT/IL2003/00983, filed Nov. 19, 2003.

International Search Report published Feb. 7, 2011 for PCT/US2010/036887, filed Jun. 1, 2010.

International Search Report published Jan. 12, 2011 for PCT/US2010/037043, filed Jun. 2, 2010.

International Search Report published Mar. 31, 2011 for PCT/US2010/036887, filed Jun. 1, 2010.

International Search Report dated Jan. 10, 2011 for PCT/US10/37043.

* cited by examiner

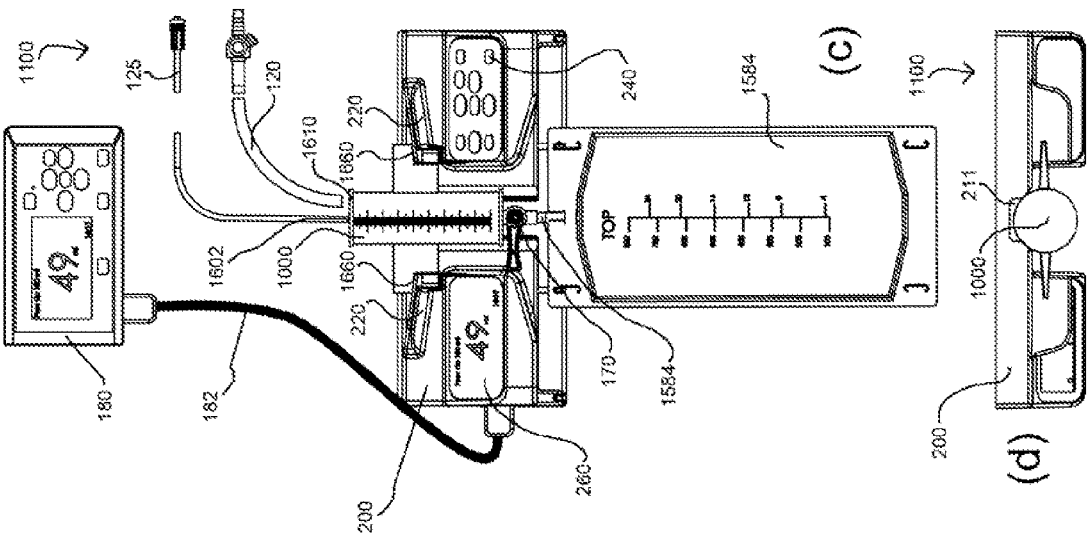
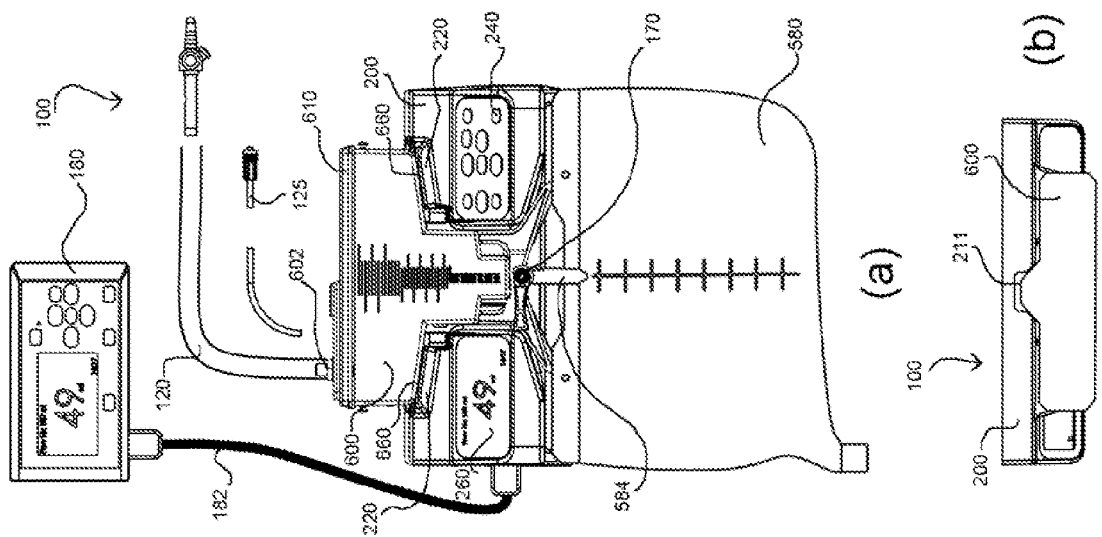
FIG.1

FIG. 4
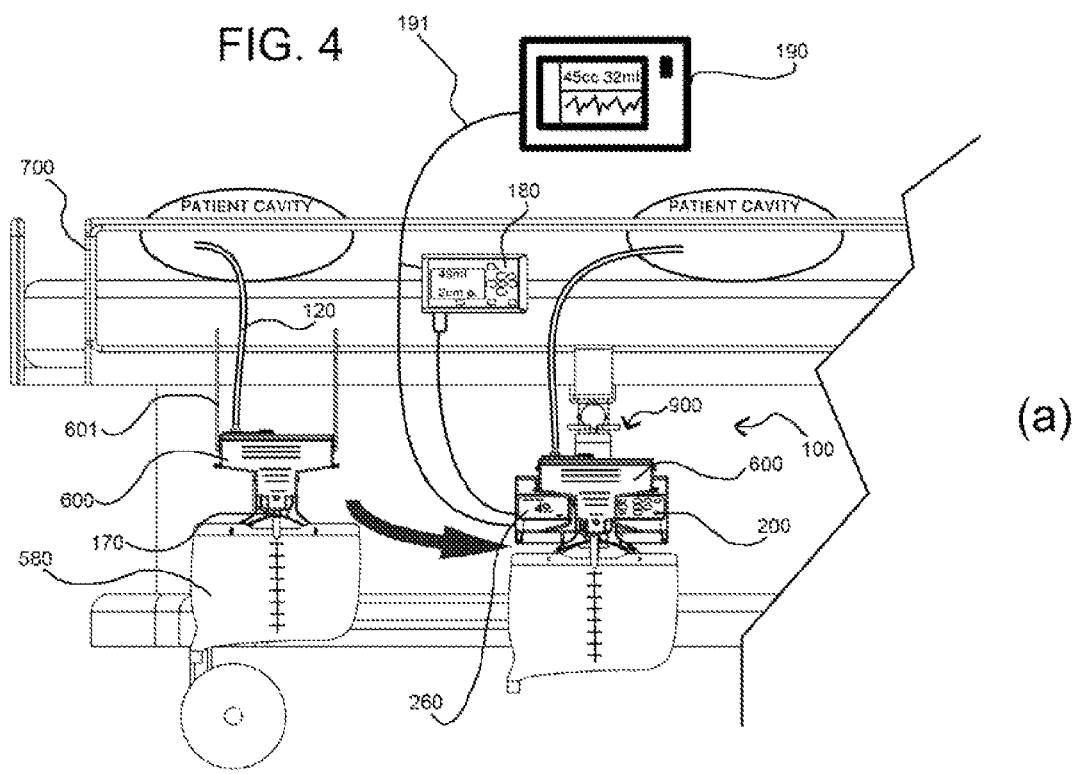
(a)
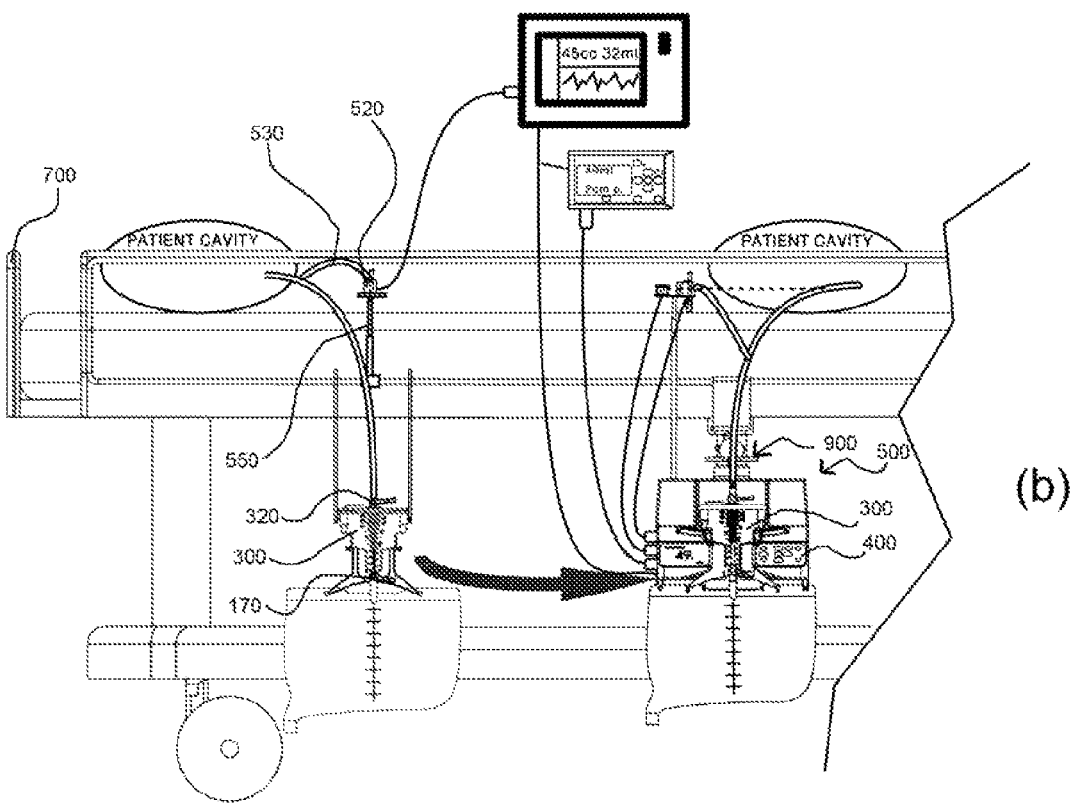
(b)

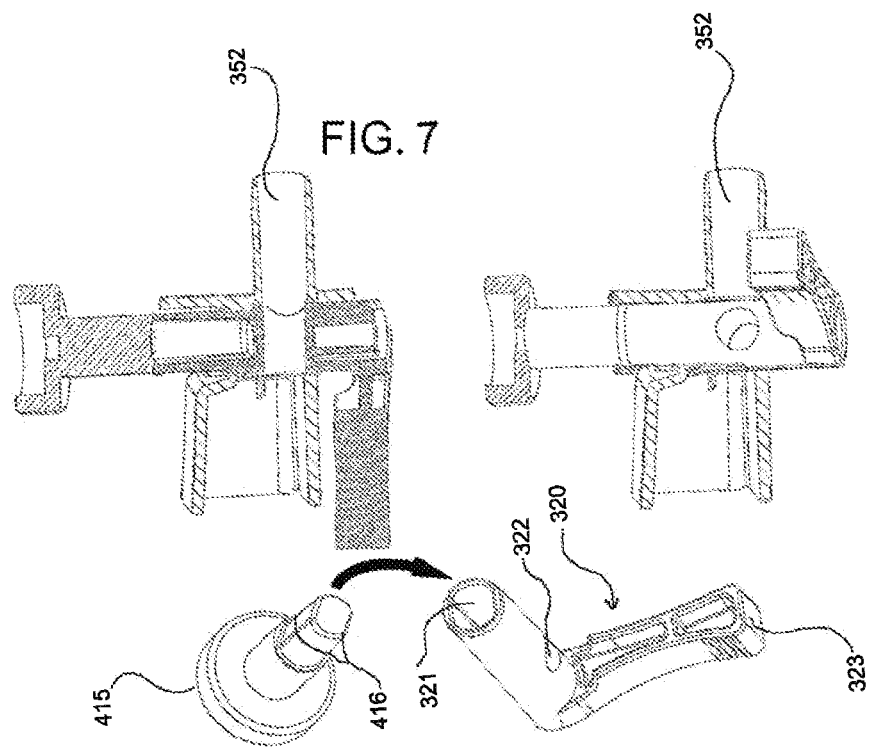
(a)
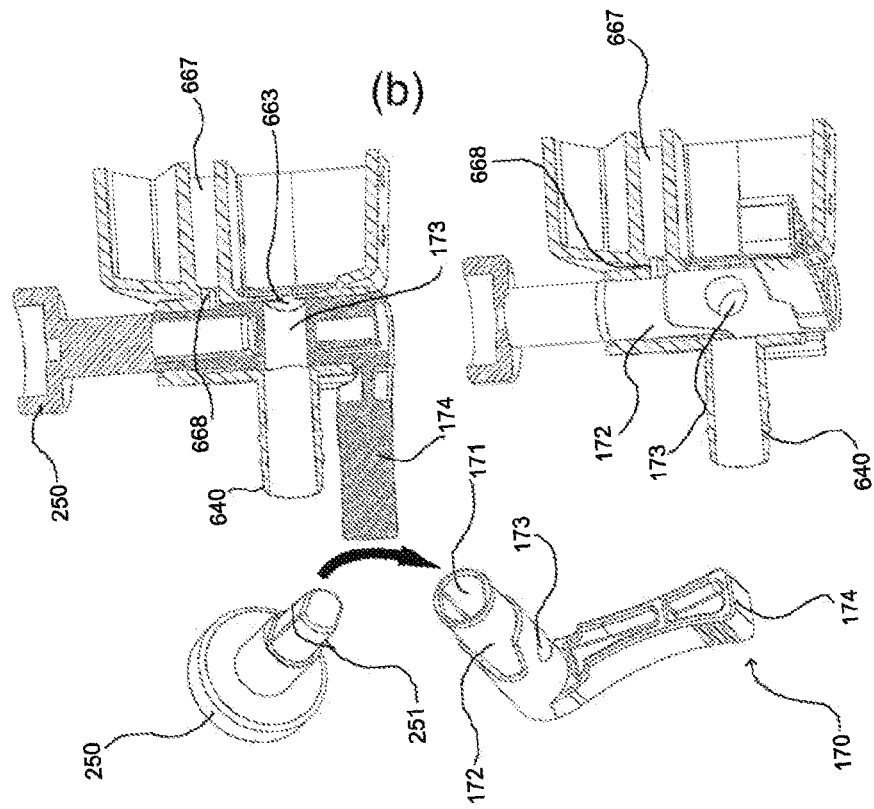
(b)
FIG. 7

FIG. 10
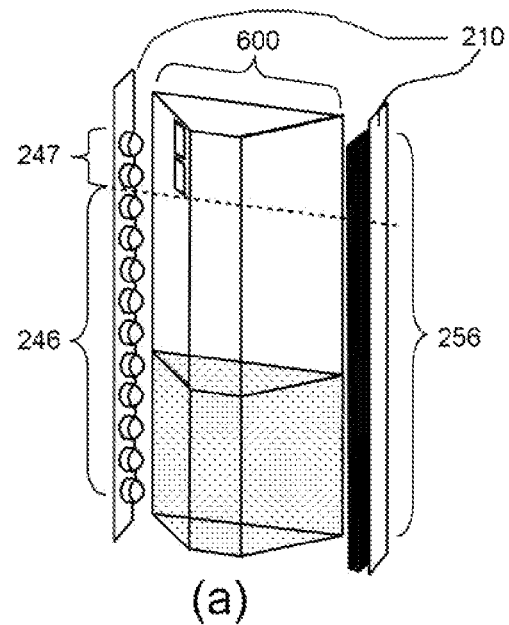
(a)
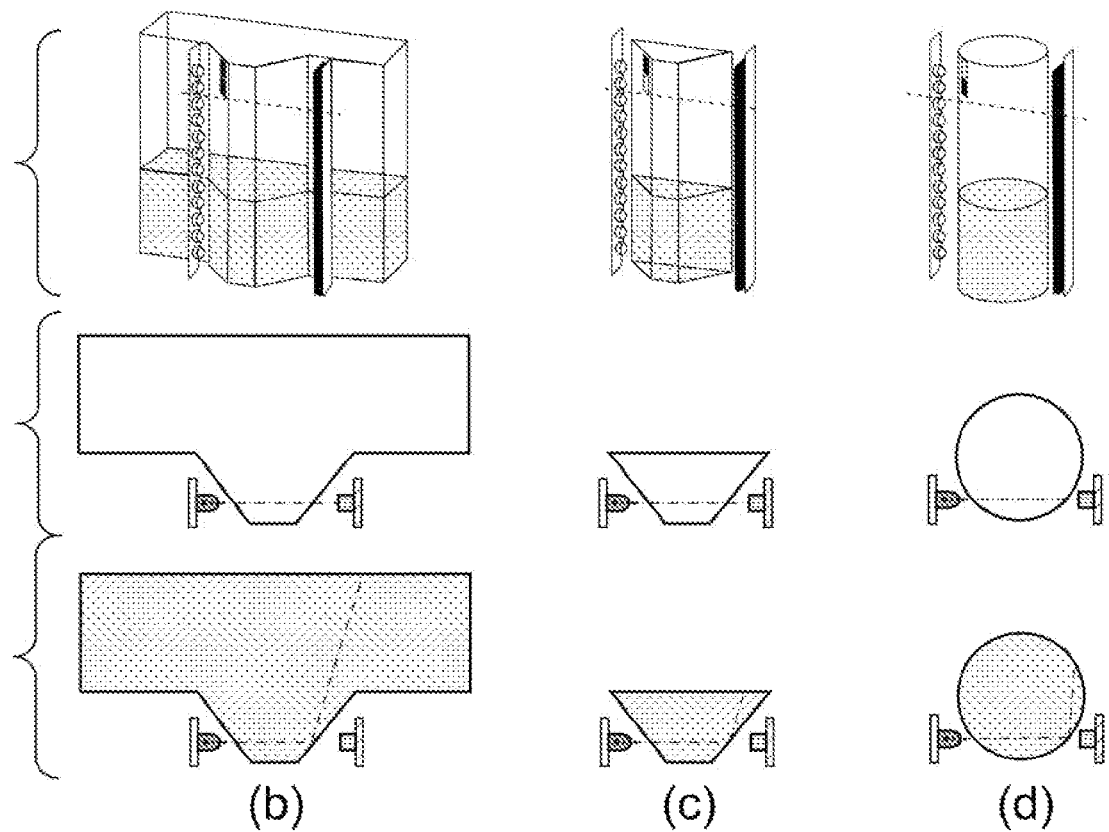
(b)  (c)  (d)

FIG. 11
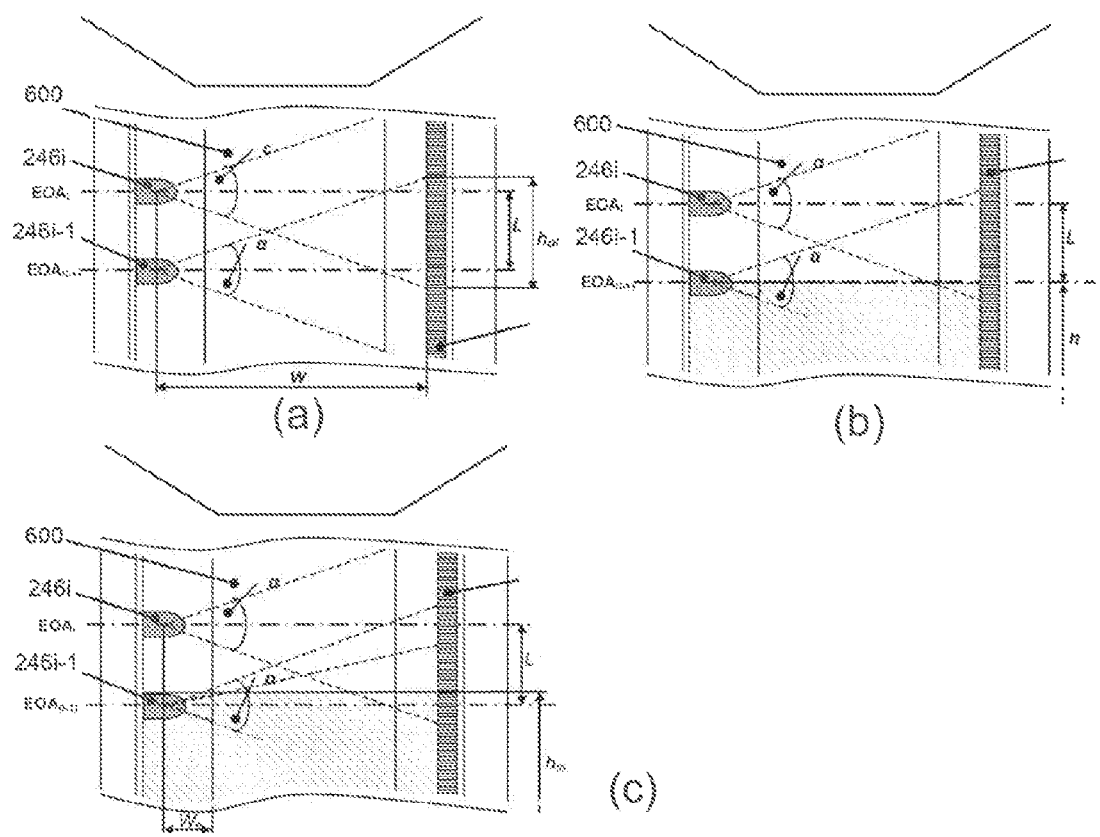
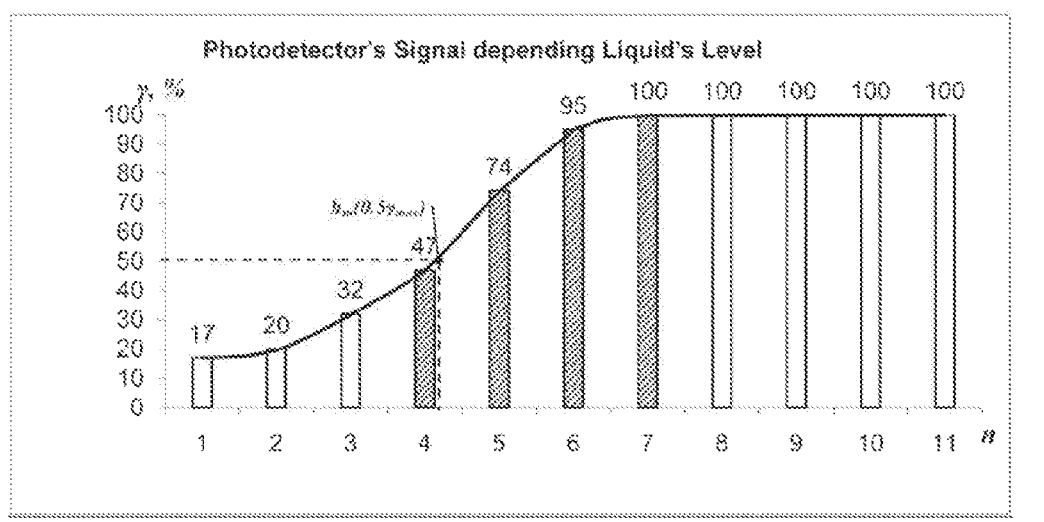

FIG. 15
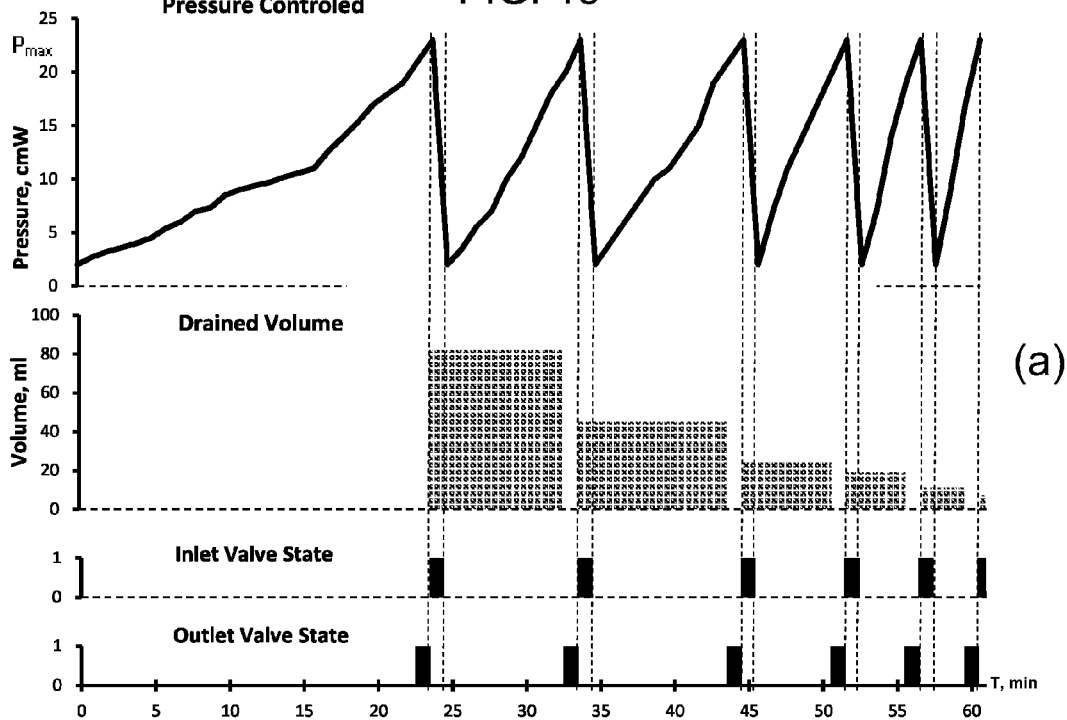
(a)
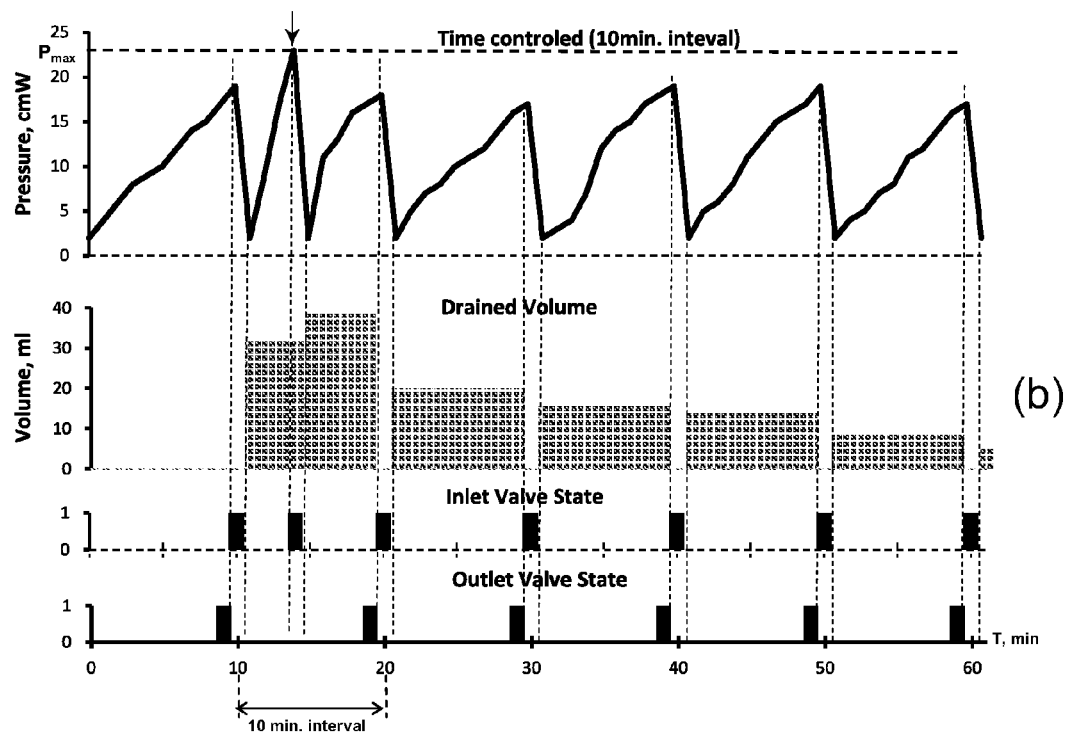
(b)

| Device mode | Event | Possible reason | Display indication |
|---|---|---|---|
| General | Vessel is not in the cradle | unit has been turned on and it the URX is not in the cradle | Insert URX |
| | Sensors do not show vessel when they should | vessel is misplaced | Check URX |
| | | vessel was removed from the cradle | Check Valve |
| | Calibration Fail | Dirty vessel | |
| | The valve is jammed or not in position | valve is not rotating as commanded | |
| | | The valve has been rotated manually. | |
| | To much environmental light | Direct sun light | Too much light |
| | Device inclined | inclination greater than corrigible | Straight device |
| Volume Measurement 31 | | | |
| Pressure 38 Measurement | Pressures level out of limits* | Measured cavity over-pressurized | Pressure Alarm* red light buzzer |
| | | DPT reading out of scale | |
| | | Inlet valve is open, No pressure drop | Check DPT* |
| | Battery voltage of the reaches limits | 20%> Bat.>10% | Low batt Icon |
| | | 10%> Bat.>5% | "Low Battery" |
| | | 5%> Bat.>1% | Automatic shut down |
| | Memory is reaching the limit | | Low memory |
| | Communication Problem | | Communication problem |

APPARATUS AND METHOD FOR BEDSIDE COLLECTION OF BODY FLUIDS AND AUTOMATIC VOLUME LEVEL MONITORING

BACKGROUND OF THE INVENTION

1. Field of the Invention

This invention relates to a bedside apparatus and method for the collecting, measuring and monitoring of the output volume of liquids, especially urine and CSF, drained from a catheterized patient, at specific medical conditions, by means of an optical refraction method with an option to monitor also pressure from the drained organ and to correlate it to the drained volume, and to a computer readable media containing programmed instructions for carrying out the steps of the method.

2. Prior Art

The importance of monitoring discharged body fluid's volume level has long been known to the medical profession. For example, low urine output in critically ill patients can be an early sign of deteriorating patient condition as a result of renal failure, high intra-abdominal pressure, or congestive heart failure even before changes in other vital signs, such as, blood pressure, temperature, pulse and respiration are observed. In addition, for a critically ill patient, changes in hemodynamic measurement of cardiac output such as arterial blood pressure, central venous pressure and left arterial pressure are meaningless, if these changes are not correlated with changes in the perfusion of major organs, such as, the kidney.

In addition to urine drainage measurement, the bladder pressure measurement can give good indication of the intra-abdominal pressure. High intra-abdominal pressure (IAP) occurs frequently in patients with acute abdominal syndromes, such as, ileus, intestinal perforation, peritonitis, acute pancreatitis or trauma. An elevated IAP may lead to intra-abdominal hypertension (IAH) and abdominal compartment syndrome (ACS). Both IAH and ACS are etiologically related to an increased morbidity and mortality of critically ill patients.

The increase of the volume within the elastic structure of the abdominal wall causes an increase of overall pressure in the cavity and organs, and it may decrease tissue blood perfusion. An increase in abdominal pressure may lead to distant effects in other parts of the body, such as increased intracranial pressure, pericardial tamponade and tension pneumothorax or extremity compartment syndrome.

Monitoring Inner Cranial Pressure (ICP) and CSF are also of vital importance due to the dangerous nature of an increase in the ICP of a patient. The cranium is a rigid container, and an increase in any of its contents—brain, blood, or CSF—will increase the ICP. In addition, any increase in one of the components must be at the expense of the other two; this relationship is known as the Monro-Kellie doctrine. Injury to the brain occurs both at the time of the initial trauma and subsequently due to ongoing cerebral ischemia. In an intensive care unit, raised intracranial pressure (intracranial hypertension) is seen frequently after a severe diffuse brain injury (one that occurs over a widespread area) and leads to cerebral ischemia by compromising cerebral perfusion.

Cerebral perfusion pressure (CPP), the pressure causing blood flow to the brain, is normally fairly constant due to auto regulation, cerebral perfusion pressure is calculated by subtracting the intracranial pressure from the mean arterial pressure: CPP=MAP−ICP. One of the main dangers of increased ICP is that it can cause ischemia by decreasing CPP. Once the ICP approaches the level of the mean systemic pressure, it becomes more and more difficult to squeeze blood into the intracranial space. As an intracranial mass lesion or oedematous brain expands, some compensation is possible as cerebrospinal fluid (CSF) and blood move into the spinal canal and extra cranial vasculature, respectively. Beyond this point, further compensation is impossible, ICP rises dramatically and only external removal of CSF can lower the ICP level.

Monitoring of CSF & Urine Output

Urine output is being measured manually by means of various measuring collecting systems. Such systems normally contains a collecting and measuring rigid transparent vessel hanged by the bedside to allow gravitational drainage, having a graduated scale and an inlet tube connected to a catheter. The measuring rigid transparent vessel has an emptying valve being connected to a secondary elastic reservoir. The liquid output volume is measured and then emptied to the secondary reservoir at predetermined hourly intervals. The above volume metering procedure also enables to visualize during the measurement intervals the optical visualized properties of the drained urine, such as, color, turbidity and possible sedimentation which gives more clinical information.

Manually Measurement of intra-abdominal pressure on a catheterized patient using the bladder is done by injecting a known quantity of saline through the Foley catheter into the bladder, then closing the drainage and measuring the pressure inside the bladder by means of pressure transducer.

Intracranial pressure is manually measured with the use of pressure transducers. A catheter is surgically inserted into one of the brain's lateral ventricles and is used to drain CSF (cerebrospinal fluid) in order to decrease ICP's. This type of drain is known as an EVD (extra ventricular drain). The CSF is drained into a rigid transparent vessel in the same manner as described above, but instead of using a gravitational drainage approach, a liquid column gauge procedure is used where the CSF drainage will be depended on the water column height, which is defined by the height of the rigid container. This drainage, as in the urine volume metering system, enables to visualize during the measurement intervals the CSF color, turbidity and possible sedimentation which provides more clinical information.

Different designs of collecting vessel, which differ in their collecting volume capacity and accuracy, are used for a variety of procedures in different hospital wards. For instance, for pediatric urine measurement a small rigid container is needed as opposed for adults where a larger container is required. Also, for intensive care units and operating rooms the accuracy of the urine drainage measurement has to be substantially higher than in other wards, therefore, the urine collecting vessel used is require to have a higher degree of accuracy. In the case of CSF drainage a small and precise collecting vessel is required.

Clinicians have been searching for a methodology for the automatic collection and data analysis of fluids outputs like Urine and Cerebrospinal-fluids (CSF) in real time. Manual procedures require measurement of contained volume by the end of a preselected time interval, thus consuming costly nursing time, and in addition risking the accuracy of the measurement due to inaccurate scale reading and non-precise following of the preselected time interval. Another factor relates to the increased risk of cross contamination due to the frequent manual operation of the system. In addition, all liquid output results are recorded manually and cannot be transferred automatically to a ward computer network unless the observed data is typed-in.

All of the above are some of the main reasons for the desirability of more accurate online electronic liquids output measuring and monitoring systems.

Electronic meters for monitoring urine output of a patient are well known and feature different measuring techniques. An ultrasonic measuring technique is shown in U.S. Pat. No. 4,448,205, U.S. Pat. No. 4,658,834, U.S. Pat. No. 5,891,051 and U.S. Pat. No. 6,582,379. In the ultrasonic systems described, the patient fluid is discharged into a container with an ultrasound transducer mounted to a housing adjacent the container and acoustically coupled to a wall of the container. When a sound wave hits the interface between the air and the liquid in the container, the signal is reflected. The measurement of the volume is being done by determining the time duration required for the transmitted energy to travel from the transducer to the upper surface of the collecting urine pool and back again.

Drawbacks of these types of measurements techniques are due to the sensitivity of the measurement. Tilting of the measuring vessel, particles such as blood in the liquid, foam and temperature changes of the liquid can all cause inaccurate readings? In addition there is a great need for transducer calibration and there might be risk of ultrasonic interference with other ultrasonic measuring devices. There is also accumulation of the drained urine without the possibility of being able to measure new fresh specimens of urine according to predetermined time intervals or desired volume quantity. As a result of this drained fluid accumulation, it is not possible to view the optical properties of the freshly drain urine which can provide additional important information.

Use of a method of weighing the body of drained fluid mass with a force transducer/weight cell is described in patents DE 3544676, EP 0242128B1, U.S. Pat. No. 5,769,087 and U.S. Pat. No. 5,776,077, where the accumulated body fluid is suspended from the force transducer/weight cell. This measurement is very much effected by the movement of the measured bag and the inclination of the bag from its horizontal state, which can easily lead to hardly detectable false measurements. Moreover, as mentioned above, the measured liquids are being accumulated with no ability to view the optical properties of fresh urine output specimens.

Using a drops counting method is described in EP 0901778A2 and U.S. Pat. No. 6,640,649B1, and requires having a drip chamber with a sensor that includes a light source located on one side of the chamber and a light detector located on the opposite side of the chamber. The system preferably includes a filter upstream of the drip outlet and some type of restriction, "drop generating orifice", to enable to "create a standard drop". The main problem with this type of method is the fact that the drained fluid can be viscose and may include foreign objects and sedimentation, which can lead to occluded filters and a blocked drop generation orifice. Furthermore, with this method, as well as with the ones mentioned above, it is not possible to view the optical properties of freshly drained urine, which can provide additional important information.

In addition to the above methods there are also optical methods, such as the one described in the U.S. Pat. No. 4,343,516. As described, there is a chamber of specific configuration having two electronic controlled valves located above and below the chamber and an optical sensor situated at the top of the chamber below the upper valve. The lower valve is closed when urine enters the chamber until the point where the urine level reaches the optical sensor at which time, by virtue of electronic control, the upper valve will close and the lower valve will open, allowing the urine to pass into a collection receptacle drainage bag. These methods have the drawback that the measurement is related to the chamber volume, so until the chamber is filled there is no possibility to know the amount of drained urine. The volume range of the chamber is usually between 5-10 cubic centimeters. In case of movement of the chamber the urine can accidently reach the optical sensor and the lower valve will be opened and the measurement will not be accurate. For the visualizing of the optical properties 10 cubic cm could be a too small volume and the "turnover" of the urine might be too fast.

Another optical method is described in U.S. Pat. No. 4,745,929. In this method, the drainage system comprises a container having a rigid conduit to receive the liquid and a receptacle to receive the urine after its accumulation in the conduit. The filling and empting of the conduit is done as in the previously described optical method, but in this method the height of the liquid in the conduit is measured. This measurement is done by using a pair of emitters (LEDs) and detectors, where the level of the liquid is detected by means of refraction. The main drawback of this method is the fact that there is no possibility to measure the liquid level when it lays in-between the pair of LEDs.

Automatic measurement of ICP & CSF can be seen in the German patent EP 174954981. In this system the CSF is pumped out in accordance to the ICP measurement. The problems with this method are, risk of accidental over pumping and that the fact that the CSF cannot be visualized, since it is drained into one container after the peristaltic pump. In addition, the measurement of the amount of CSF is calculated from the number of turns of the peristaltic pump, according to the tubing size used, which leads to inaccurate readings due to changes in the tube.

SUMMARY OF THE INVENTION

This invention relates to a bedside apparatus and method for the collecting, measuring and monitoring of the output volume of liquids, especially urine and CSF, drained from a catheterized patient, at specific medical conditions, by means of an optical refraction method with an option to monitor also pressure from the drained organ and to correlate it to the drained volume. The liquid drained from a patient can be drained from an orifice, such as the drainage of urine by using a Foley catheter, or from a patient cavity, such as drainage of excess CSF by using a ventricular drain.

More specifically, the invention relates to a medical apparatus and method that electronically measures and displays the discharge of body fluids. The apparatus is comprised of a reusable electronic housing and a disposable plastic container adapted to be received and removed from a cavity defined by the electronic housing. The liquid output is measured outside or externally of the disposable container, by using a novel optical level metering system. The disposable container has a measuring scale and inlet and outlet stopcock like valves that engage or couple with shaft like connector endings of electrical motor drives, which in turn, enables to open and close the flow of drained fluids into an out of the container automatically. The opening of the outlet valve enables the emptying of the container to an elastic accumulation drainage bag.

This novel disposable container is designed in a way that it can also be manually operated or viewed in order to monitor the process of body fluids drainage. This way, the disposable part of the apparatus can be operated or viewed manually, and when a more exact monitoring is needed, it can be plugged into the reusable electronic system, or the reusable electronic system can be activated, for automatic monitoring without the need to disconnect the patient. Vice versa, when there is no more need for automatic measurement, the disposable system can be disconnected or deactivated from the reusable electronic system and manual monitoring can be resumed. This feature is not available in any of the prior art.

Also within the scope of this invention, the drained liquid is measured in the collecting container until it reaches a predetermined height or reaches the end of a preset time interval. The height and time intervals can be adjusted to any time interval and/or accumulated volume protocol according to the clinical procedure needs. This adjustment cannot be done in any of the prior art.

Furthermore, while plugged in or activated to automatically measure and monitor the liquids output volume, the apparatus and method mimics currently used clinical procedures of urine and CSF volume metering, enabling the clinical staff to view other collected fluid characteristics like color, which can indicate blood in the liquid, turbidity, sedimentation and ease of aspirating sampling of liquid at any given time interval. These features are lacking in the majority of the prior art, where the drained body liquid is being continuously accumulated and visualizing the liquid in relation to time intervals is not possible.

The apparatus and method measures and monitors the liquid output volume in the collecting container by means of a novel optical refraction method using a specific algorithm. The apparatus is capable to identify the height of any collected liquids, from the bottom of the disposable container to the highest limit of the optical segment (height of the facing and vertically parallel LEDs and photo detector arrays). The particular measuring technique of the present invention for determining the liquid's surface height is accomplished by scanning the space of the transparent measuring vessel or collecting container that is placed between a vertically oriented array of light emitters and an elongated photodetector. The scanning is based on the refraction of the emitters' rays on the boundary of two medias due to the special measuring vessel's (collecting container's) construction.

The scanning is accomplished by the reusable electronic component that contains a specially designed optical cavity for receiving and holding the collecting container in a proper orientation. The optical scanning, as noted above, comprises an optical segment composed of a vertically oriented LED emitter array and an elongated vertically oriented photodetector, both of which are positioned vertically facing each other and horizontally spaced in such a way that whenever the collecting container or vessel is mounted and held in the cavity defined by the reusable electronic unit or component, the optical part of the collecting container or vessel is vertically situated between the array of LED emitters and the photodetector. The height of the optical segment of the reusable electronic component extends the entire height of the optical portion of the collecting container or vessel and the light emitted by the LED emitters of the array are transmitted through the optical portion of the measuring collecting container or vessel.

The reusable electronic unit or component thus functions to detect continuously the height of the collected liquid column in the collecting container or vessel by means of the photodetector, which produces an output indicative of the intensity of the detected light.

Due to the inventive apparatus and method of measuring liquid level height, the measurement can be done regardless of the characteristics of the liquids. The apparatus will function in the very same manner at different liquid temperatures, in case of clear transparent up to highly dense dark liquids, with different fluid viscosities or weights, and also in cases where the fluids contains high contents of colloid particles, such as blood clots, that can emerge in the CSF, or some sedimentation that can appear in the urine, regardless of the shape and size of the particles.

Since different requirement are demanded in different hospital wards (adult and pediatric intensive care, general and neurosurgical intensive cares), different designs of the collecting vessel with different capacities are required in order to provide higher, lower or variable resolution of the fluid column, different sampling ports, and other features as will be evident from the following detailed description. The present invention functions with different designs of collecting vessels and the apparatus and method have the capability to "recognize" the particular type of collecting vessel being used by means of a novel optical technique.

In the apparatus and method of the present invention the electronic system, the same disposable container and elastic or flexible bag is used and an emptying valve is opened automatically on a preselected time basis, for example, an hourly basis, or responsive to the liquid having accumulated to a predetermined level.

The container includes hangers for holding the elastic or flexible bag. Thus, the elastic or flexible bag can be exchanged without the need to disengage the container from the electronic reusable part. This is an advantage over most automatic drained liquid measuring apparatuses, where, when the disposable container is full there is a need to stop measurement and exchange the disposable container. In this inventive apparatus and method there is not such a need because the measurement is done outside or externally of the container, which allows the elastic or flexible bag to be exchanged without affecting the level measurement that is being carried out relative to the container. In addition, since the container has a novel overflow feature, similar but different to manually designed containers currently in use, when the drained liquids are being accumulated and there is a malfunction in the automatic valve opening, the novel overflow design enables excess liquids to drain into the elastic or flexible bag, as opposed to other automatically monitoring apparatuses that do not posses such a characteristic of the disposable container part.

It is further in the scope of this invention that the accumulation of fluid can be done continuously as described above or in relation to pressure measurement from the drained area. In order for this aspect of the invention to perform, the inlet of the drained liquids to the container is blocked using an upper stopcock like valve in addition to the lower valve. This upper valve can prevent the drainage of the liquids and enable the pressure accumulation in the drained organ, such as the bladder, which gives an indication of intra-abdominal pressure, or the cranial cavity, giving an indication of the inner cranial pressure (ICP). The upper valve is opened automatically according to a predetermined pressure or a predetermined time. In either case the pressure is continuously measured. In addition, after opening the upper valve, the amount of drained liquid is recorded. The pressure measurement in correlation with time and liquid accumulation can give indications of different medical conditions, both in intra-abdominal pressure measurement and in CSF/ICP measurements.

As mentioned above, the correlation between time, pressure and volume of the drained liquid can give good indication of the patient clinical situation. For example, in intra-abdominal pressure measurement, if there is a rapid elevation of the measured pressure (above 15 mm Hg) in a short time, compounded with a very low urine volume output, one can suspect an abdominal compartment syndrome. Vice versa, for the same time intervals and the same pressure elevation, if the urine output is high, then one will not suspect any difficult clinical condition. As the abdominal compartment syndrome is treated, the same bladder pressure will be reached after longer time intervals and the urine volume output will increase.

In another example, for ICP/CSF correlation the situation is somewhat different. Elevated ICP (above 20 mm Hg) is correlated with high volume of drained liquid, such as CSF or blood. The lower the ICP measurement in the same time intervals with decreased liquid drainage volume can indicate a recovery of the patient, due to less bleeding or resume possibility for CSF absorption.

Other and further objects and advantages of the apparatus and method of the present invention will become apparent from the following detailed description of preferred embodiments of the invention when taken in conjunction with the appended drawings

BRIEF DESCRIPTION OF THE DRAWINGS

FIGS. 1(a) to (d) show schematically in a front view two preferred embodiments of a single motor valve Fluid Secretion Pressure Monitor (FSPM) apparatus according to the present invention.

FIGS. 4(a) to (b) show schematically in front view how the Fluid Secretion Pressure Monitor (FSPM) apparatus of the present invention can be adapted for converting urine output and intra-abdominal pressure measurement procedures to automatic procedures.

FIGS. 7(a) to (b) show schematically and partially in section views of the inlet & outlet valves of a FSPM apparatus according to the present invention in their open & closed positions and how the shafts engage

FIGS. 10(a) to (d) show schematically the optical unit of the present invention and illustrates how liquid level and identify the type of vessel mounted on the electronic unit is determined.

FIGS. 11(a) to (d) are further schematic views and a graph illustrating in more detail the operation of the optical unit of the present invention.

FIG. 18 is a block diagram showing details of the software warnings and alarms.

DETAIL DESCRIPTION OF PREFERRED EMBODIMENTS OF THE INVENTION

Figure 2:
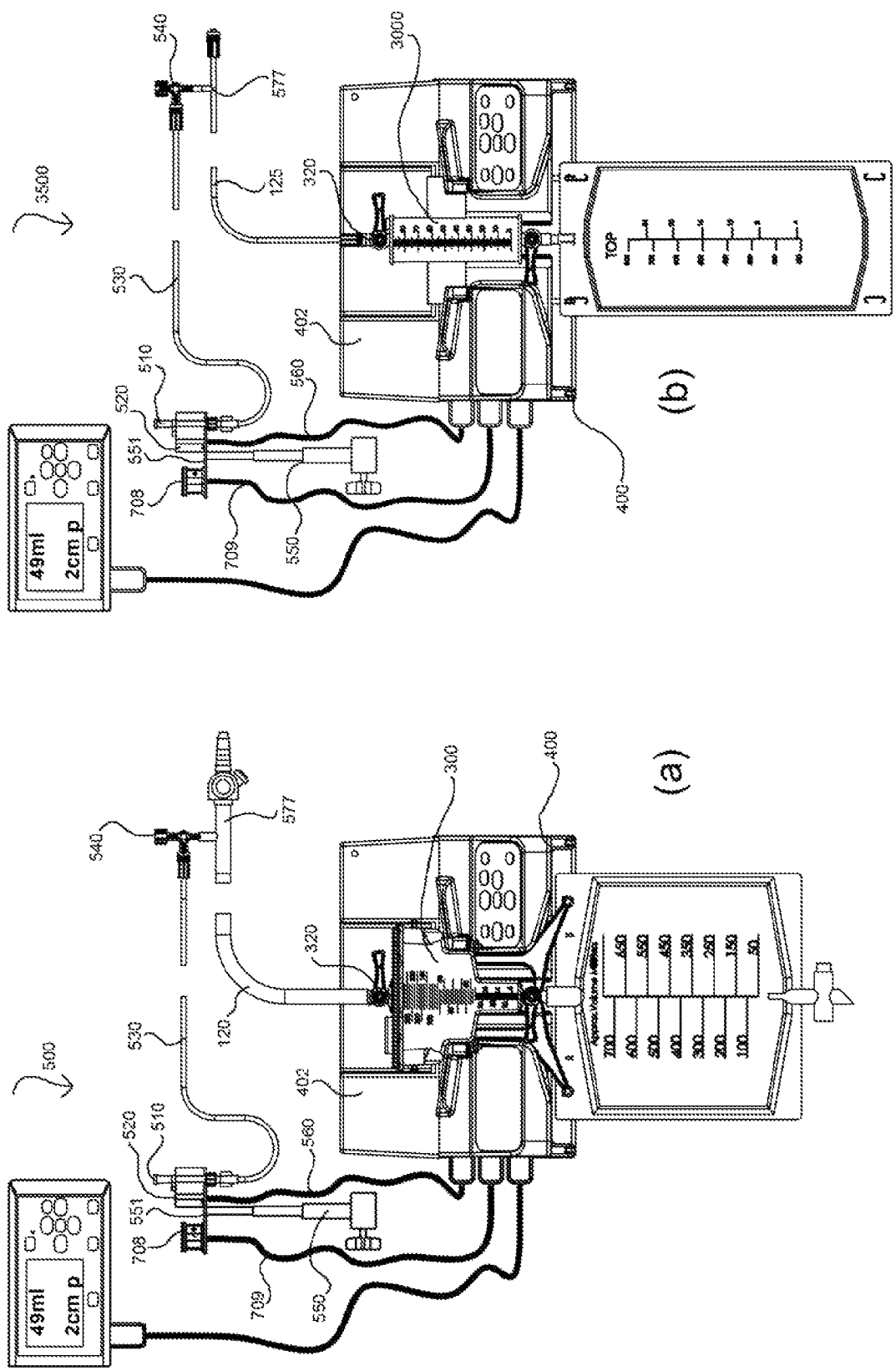
FIGS. 2(a) to (b) show schematically in a front view two preferred embodiments of a double motor valve Fluid Secretion Pressure Monitor (FSPM) according to the present invention.

Referring now to the drawings preferred embodiments of the present invention will now be described in detail. Referring initially to FIG. 1, two preferred embodiments of a single motor valve Fluid Secretion Pressure Monitor (FSPM) apparatus according to the present invention are shown, namely, preferred embodiment of the Fluid Secretion Pressure Monitor (FSPM) apparatus, FIGS. 1 (a & b) 100 and preferred embodiment of the Fluid Secretion Pressure Monitor (FSPM) apparatus, FIGS. 1 (c & d) 1100. The two embodiments measure, in an automatic way, accumulated liquids in disposable vessels having a single motor for operating in an electromechanically way the outlet valve of the disposable vessels, which will be explained in detail hereafter. The opening of the outlet valve is fluid level depended and time as will hereafter be explained in detail.

The two preferred embodiment of FIG. 1 have the same electronic unit 200 with two different disposable collecting plastic vessel containers. In FIG. 1 (a) a rectangular shaped container 600 can be seen and in FIG. 1(c) a burette type container 1000 can be seen.

The collecting vessel 600 has a cover 610 provided with an inlet 602, the corresponding burette type 1000 has a cover 1610 provided with an inlet 1602. Coupled to the upper inlet 602 &1602 is a high flow drainage tube 120 or alternatively, a low flow drainage tube 125. The use of a high or low flow drainage tube depends on the liquid draining. For example, for urine a high flow tube is used whereas for CSF a low flow tube is used. Both containers are provided with a shoulder like area, 660 in vessel 600 and 1660 in burette 1000. The shoulder areas serve to mount the vessels on mounting ledges 220 of electronic unit 200. Both disposable vessels have the same outlet valve 170. A secondary flexible reservoir 580 of vessel 600 and secondary reservoir 1580 of vessel 1000 are connected via an inlet port 584 and 1584, respectfully, that engages with lower outlet connector, (not shown) of the collecting vessel 600 and 1000, respectfully. In FIG. 1 display panel 260 and control panel 240 of electronic box 200 can be seen. An optional remote control and display unit 180 can be also seen connected to the electronic unit 200 by an appropriate cable 182. In FIGS. 1b and 1d, top views, shows the disposable vessels inter-engaged with optical segment cavity 211 of electronic unit 200, which will be explained in further details with respect to the FIGS. 3 & 6 and FIG. 10.

Referring now to FIGS. 2(a) and (b), two preferred embodiments of a double motor valve Fluid Secretion Pressure Monitor (FSPM) apparatus are shown, namely, in FIG.

2(a) 500 and in FIG. 2(b) 3500.d This apparatus measures in an automatic way the accumulated liquids of disposable vessels having a double motor for operating in an electromechanically way the outlet & the inlet valves of the disposable vessels, which will be explained thereafter. In FIG. 2 the two preferred embodiments of the Fluid Secretion Pressure Monitor (FSPM) apparatus the opening of the inlet valve is pressure & time dependent and the opening of the outlet valve is fluid level & time dependent.

The two preferred embodiments of FIG. 2 use the same FSPM unit 400 with two different disposable collecting plastic vessel containers. In FIG. 2(a) small rectangular shaped container 300 can be seen and in FIG. 2(b) a burette shaped container type 3000 can be seen. The collecting vessels 300 & 3000 have the same inlet valve 320. In addition to the inlet valve there is a telescopic pole or rod 550 that can be attached to the bed frame or can be mounted on or be a part of the electronic unit box housing 402. On the rod there is a stand 551 for mounting a pressure transducer 520 and a height beam indicator 708. The telescopic rod 550 can be adjusted so that pressure transducer (DPT) 520 and height beam indicator 708 can be at the level of the patient's drained cavity. The drainage tube, either high-flow 120 or low-flow 125, is branched at 577 via a stopcock 540. The stopcock 540 is connected to the DPT 520 via a conduit or tube 530. The DPT 520 is provided with a priming port 510. The DPT 520 functions for converting pressure sensed to a corresponding electrical signal indicative of pressure sensed and outputs a signal via DPT cable 560 to the electronic unit 400 for processing. The height beam indicator 708 gets its power supplied from the electronic unit 400 via cable 709. All other features are the same as for the single valve FSPM units.

The overall operation of the Double motor FSPM apparatus is as follows. The double motor FSPM is first placed besides the patient at a convenient height where the DPT 520 can be raised or lowered to the level of the organ to be drained by means of the telescopic rod 550. After the mounting the FSPM and the DPT is at the appropriate levels, the DPT line 530 is primed with saline through the priming port 510 while the stopcock 540 is at the open position towards the outlet of the drainage tube. Zeroing of the pressure transducer is done and the drainage tube is connected to the patient via a catheter (not shown). The unit can be powered on and the patient's bio-fluids drainage and cavity pressure measurements can be initialized as will be explained in detail with reference to flow charts illustrated in FIGS. 15 & 19 and in FIGS. 20 & 21(a).

Figure 16:
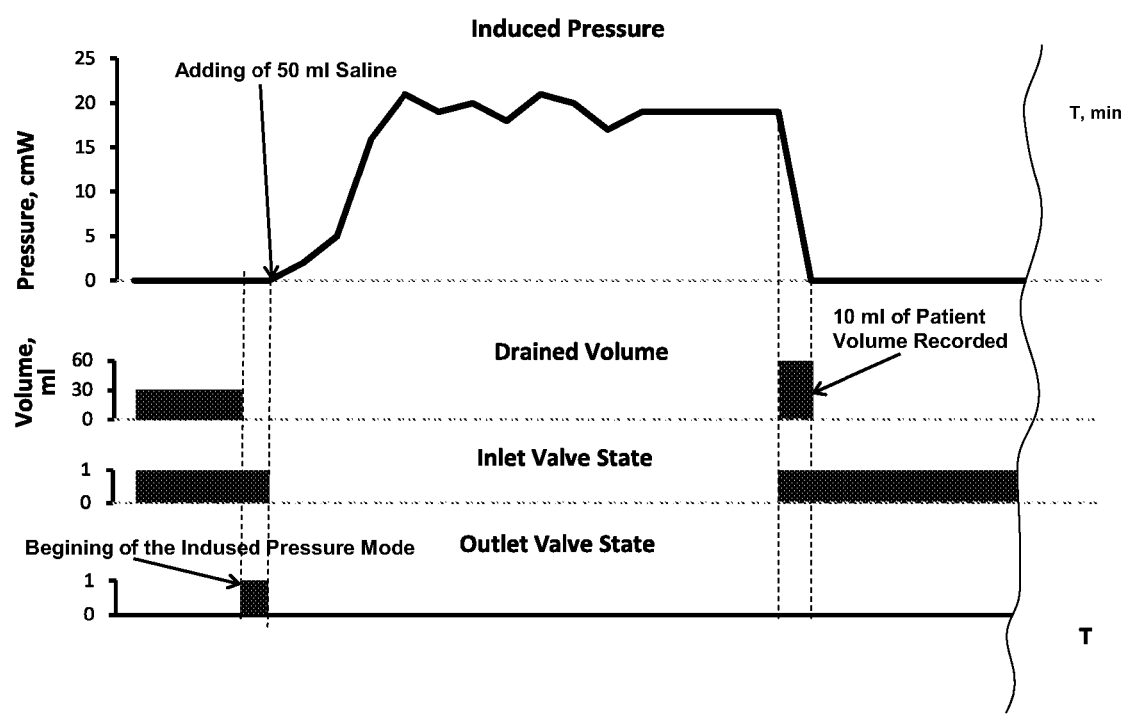
FIG. 16 is a graph illustrating the induced pressure mode of operation.

In addition to automatic measurement of pressure where the drained fluid is accumulated in the drained cavity, there is additional way of measuring pressure, especially intra-abdominal pressure, by adding a predetermined fluid, testing the intra-abdominal pressure & then opening inlet valve for drainage either in an automatic way or by pressing a button that opens the inlet valve, see flow chart illustrated in FIGS. 16 & 21b.

Figure 3:
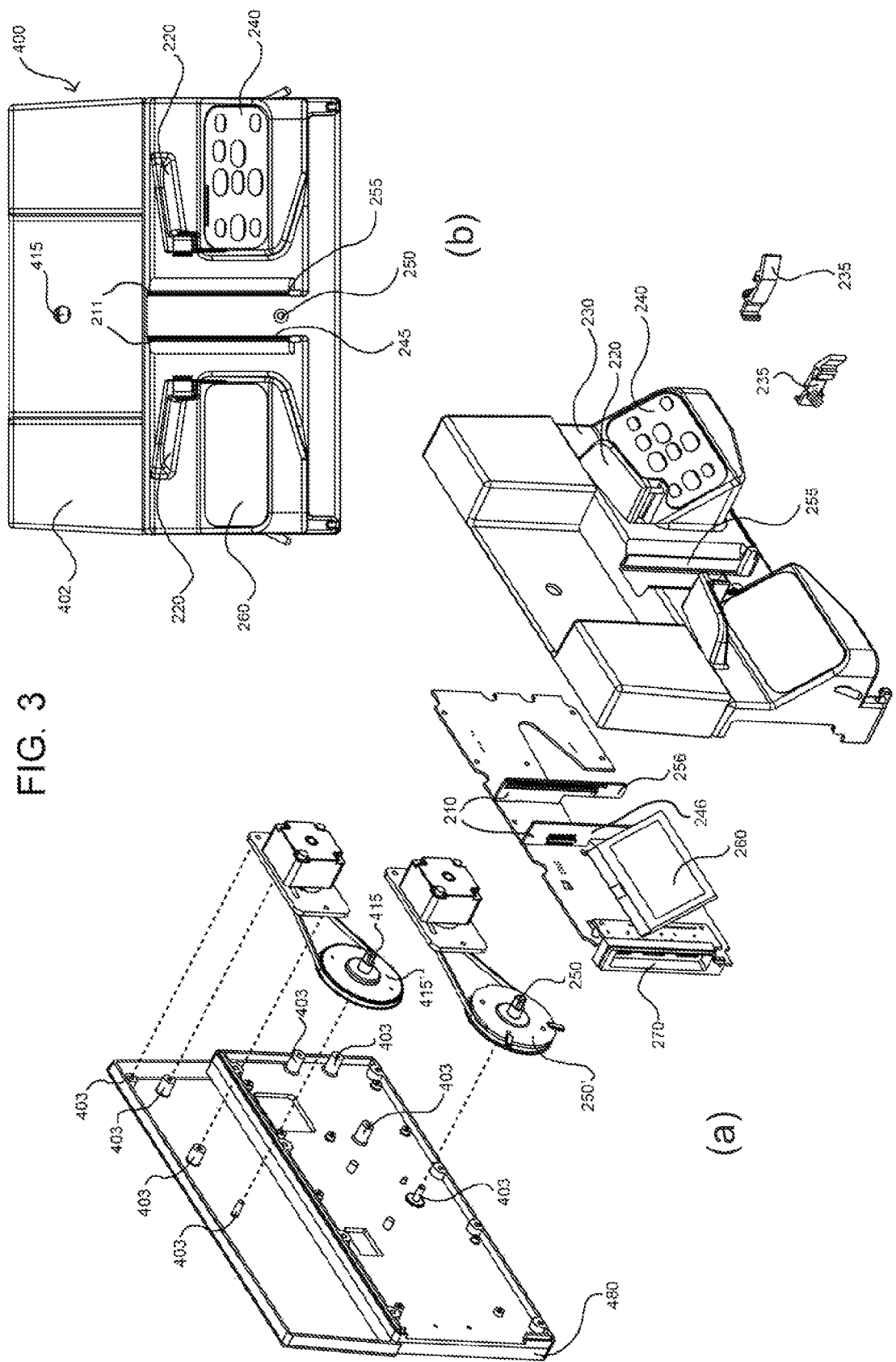
FIGS. 3(a) to (b) show a double valve Electronic unit used in the Fluid Secretion Pressure Monitor (FSPM) of FIG. 2 in an exploded view and in an assembly view.

FIG. 3 shows a double valve Electronic unit according to the present invention. FIG. 3 depicts the electronic unit 400. Unit 400 consists of a housing 402 preferably of metal or molded from a suitable plastic or a combination thereof wherein housing 402 has a back cover 480 and a front cover 230. The front cover 230 in its middle portion defines an optical segments cavity 211 of U-shaped configuration for optical segment 210. The legs of the configuration define opposite vertical slits 245 and 255. Behind slit 245 is positioned a series or array of LEDs 246 mounted in housing 402 and arranged in a vertical row to shine their light out slit 245. Behind slit 255 is positioned a photo-detector strip 256 aligned with the LEDs to receive the light emanating out of slit 245. The top two LEDs serve to identify the type of collection vessel mounted onto the electronic unit, as will be explained in greater detail hereinafter in FIGS. 10 and 12(a) to (f). Housing 402 has upper mounting ledges 220 inclined downwardly toward each other such that all types of collection vessels as can be nested. When collection vessels are nested in housing 402, their hind part is situated into the optical segments cavity 211 as to allow light from the LEDs behind slit 245 to pass horizontally through the collection vessel on path to the photo-detector behind slit 255. This mechanism will be explained in more detail in FIG. 9-12.

Clamping brackets 235 are mounted on the front of housing 402 and located just below the proximal ends of the inclined upper mounting ledges 220 such to maintain alignment and juxtaposition to side notches or projections of any of the disposable containers. When the tabs of the clamping brackets 235 are manipulated, the brackets 235 lock into the side notches or projections to securely hold the collection vessels in proper position. The conjunction of the electronic unit & the disposable vessel will be described in greater details with reference to FIG. 6.

A cable plug or terminal box in segment 270 is present on the left side wall of housing 402 and serves the purpose of providing a connection terminal for cables interconnecting the electronics of the electronic unit 400 with external functions, such as, the DPT 520 cable 560 & the height beam indicator 708 power supplied cable 709, an optional remote control and display unit 180 and an optional PC/monitor or any other patient monitoring system(s) and in addition to supply power to the system and recharge the battery 2000. A display LCD panel 260 is mounted in the housing 402 in an inclined manner on the left side of the front of the housing 402, for the purpose of displaying information under the control of the electronics contained in the housing 402. A control panel 240 with control buttons is mounted in the housing 402 in an inclined manner on the right side of the front of the housing 402, for the purpose of providing a means to control the electronics contained in the housing 402.

The connections and operation of the inlet and outlet valves includes a shaft's engagement segment 250 and its electromechanical driver 250' positioned as indicated by dashed line and anchored by snap array 403. Wherein the lower snap array 403 correspond with the lower shaft engagement segment 250 and electromechanical—the name driver 250' and the upper snap array 403 correspond with the upper shaft engagement segment 415 and electromechanical driver 415'.

For a one-valve system, electronic unit 400 does not include any parts or features from above the upper mounting ledges 220 namely the upper shaft engagement segment 415 and electromechanical driver 415.

The coupling of shaft's engagement segments 250 and 415 to vessel valves is explained in greater detail with reference to FIG. 6.

FIGS. 4(a) and 4(b) show how the currently used urine output & intra-abdominal pressure measurement procedures are converted to automatic procedures. FIG. 4(a) depicts urine drainage procedure, and FIG. 4(b) depicts the urine drainage procedure with the possibility to measure intra abdominal pressure which is a reflection of the pressure measured in the bladder.

In FIG. 4(a) a typical hospital bed 700 is shown. On the left side, a manual operated disposable Drainage device 600 is and is currently used for measurement of the urine output via a drainage tube 120. The device is hung on the hospital bed using hanging straps 601 or in any convenient other means from the frame of the bed below the drained patient cavity, the bladder. In the manual procedure urine is drained and accumulated in the disposable rigid container 600, every hour on the hour a nurse comes, measures the accumulated urine, writes it in the patient chart, open the outlet valve 170 and urine will be drained from the rigid container to the secondary flexible reservoir 580.

On the right hand side of the bed the FSPM a single motor apparatus 100 is hung via a hanging mechanism 900, which will be explained in greater details with reference to FIG. 8. FSPM apparatus 100 is comprises of the manual drainage device 600, plugged in the electronic 200 unit, thus converting the same manual procedure to an automatic one, by measuring the accumulated urine in the disposable container via a level detection mechanism that will be explained in further details in FIGS. 9-12 & 14 & 19-20 displaying the measurement on the electronic unit display panel 260 and/or remote control and display unit 180. The electronic unit 200 and the remote unit 180 can be connected via communication cable 191 to a PC, monitor or to any other patient monitoring system 190.

FIG. 4(b) shows the possibility of urine drainage with intra-abdominal pressure measurement. On the left side, a manual operated disposable drainage device 300 is hung on the hospital bed 700 using hanging straps 601 or any other means for hanging, to hang the disposable drainage device below the drained patient cavity, the bladder. In addition to the outlet valve 170 there is an inlet valve 320. In addition to the inlet valve, a pressure transducer 520 is mounted on telescopic pole 550 that can be adjusted to the level of the patient's drained cavity. A DPT is connected via tube 530 to the drainage tube 120, thus when closing the inlet valve 320 in container 300 enabling the measurement of the bladder pressure, which gives an indication of the intra abdominal pressure, the pressure of the abdomen can be measured due to accumulation of fluid in the bladder by the patient's own urine or can be induced due to predetermined fluid insertion. On the right hand side of the bed 700, the FSPM double motor apparatus 500 is hung via the same hanging mechanism 900 as above. FSPM unit 500 is comprised of the manual drainage device 300, plugged into the electronic 400 unit, thus converting the same manual function to an automatic procedure, in additional to measuring the accumulated urine, the intra abdominal pressure can be measured in an automatic way when closing the inlet valve 300 in the disposable as described with reference to FIGS. 2, 13, 19, 20 and 21.

Figure 5:
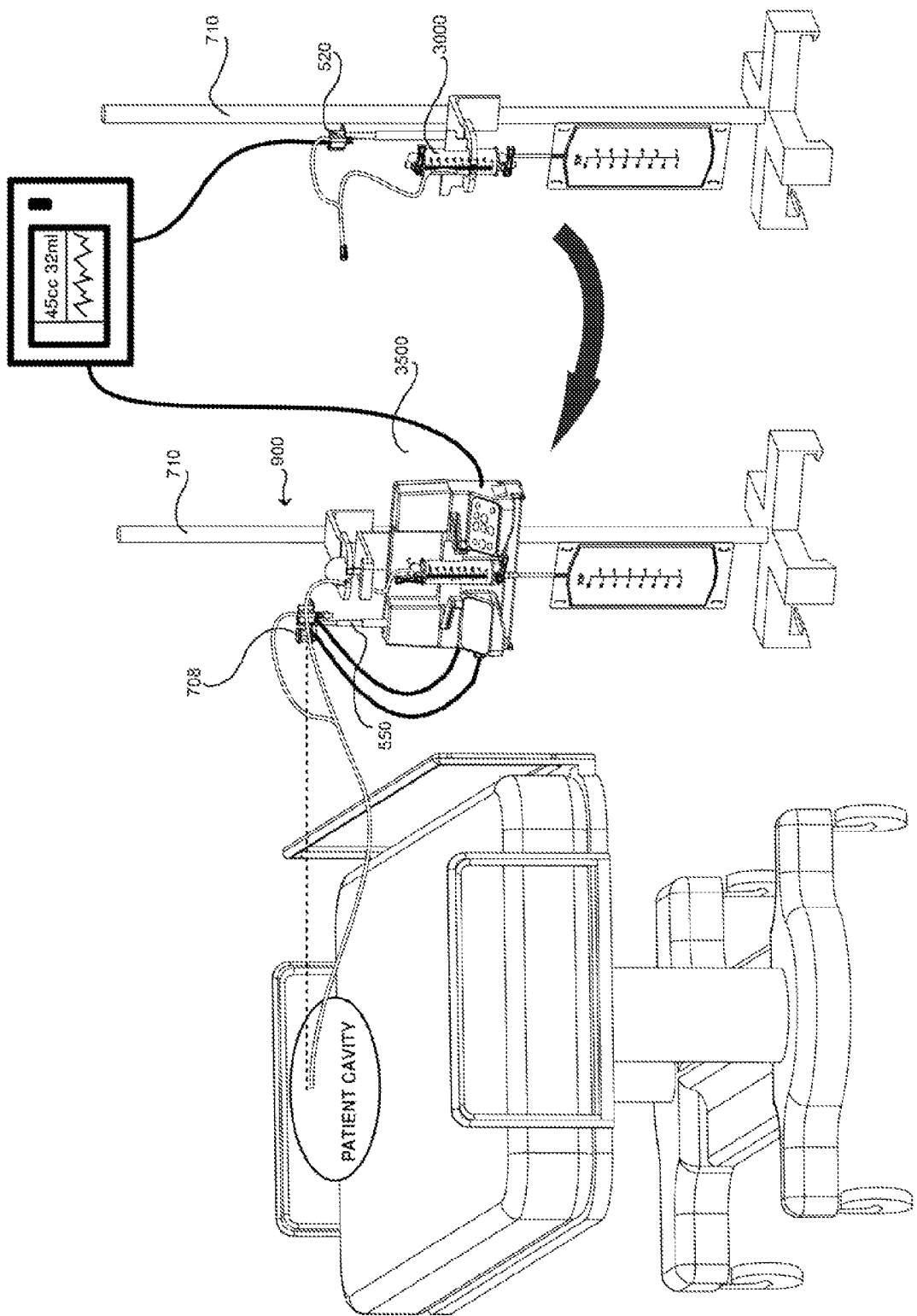
FIG. 5 shows schematically in front view how a manual measurement of an ICP (intracranial pressure) measurement and CSF (Cerebrospinal Fluid drainage) manual measurement is converted to automatic measurement by the apparatus of the present invention.

Shown in FIG. 5 is the manner of converting the currently used ICP—(intra-cranial pressure) measurement and CSF—(Cerebrospinal Fluid drainage) manual measurements to automatic procedures. On the right hand side can be seen a double valve manual burette disposable container 3000. The unit is vertically adjustable and fixable by conventional known means on a hospital stand pole 710. The burette 3000 is connected to a DPT 520 via a tube connected to the drainage tube in the same way as previously explained regarding the manual procedure. On the left hand side, closer to the bed, is the FSPM double motor apparatus 3500 mounted on a hospital stand pole 710 via hanging mechanism 900 comprises of the same manual burette 3000 plugged in with the double motor electronic unit 400. Pole 550 is fixable and mounted on the electronic unit 400, having a height level indicator 708 and pressure transducer 520. The components are connected in the same manner as described with respect to FIG. 4b. This shows the manual procedure to measure ICP and to drain the CSF according to the pressure measured, thus opening the inlet valve of the disposable container 3000, manually or automatically when measured pressure is above the threshold measurement, this will be explained in greater details hereafter in FIG. 15.

Figure 6:
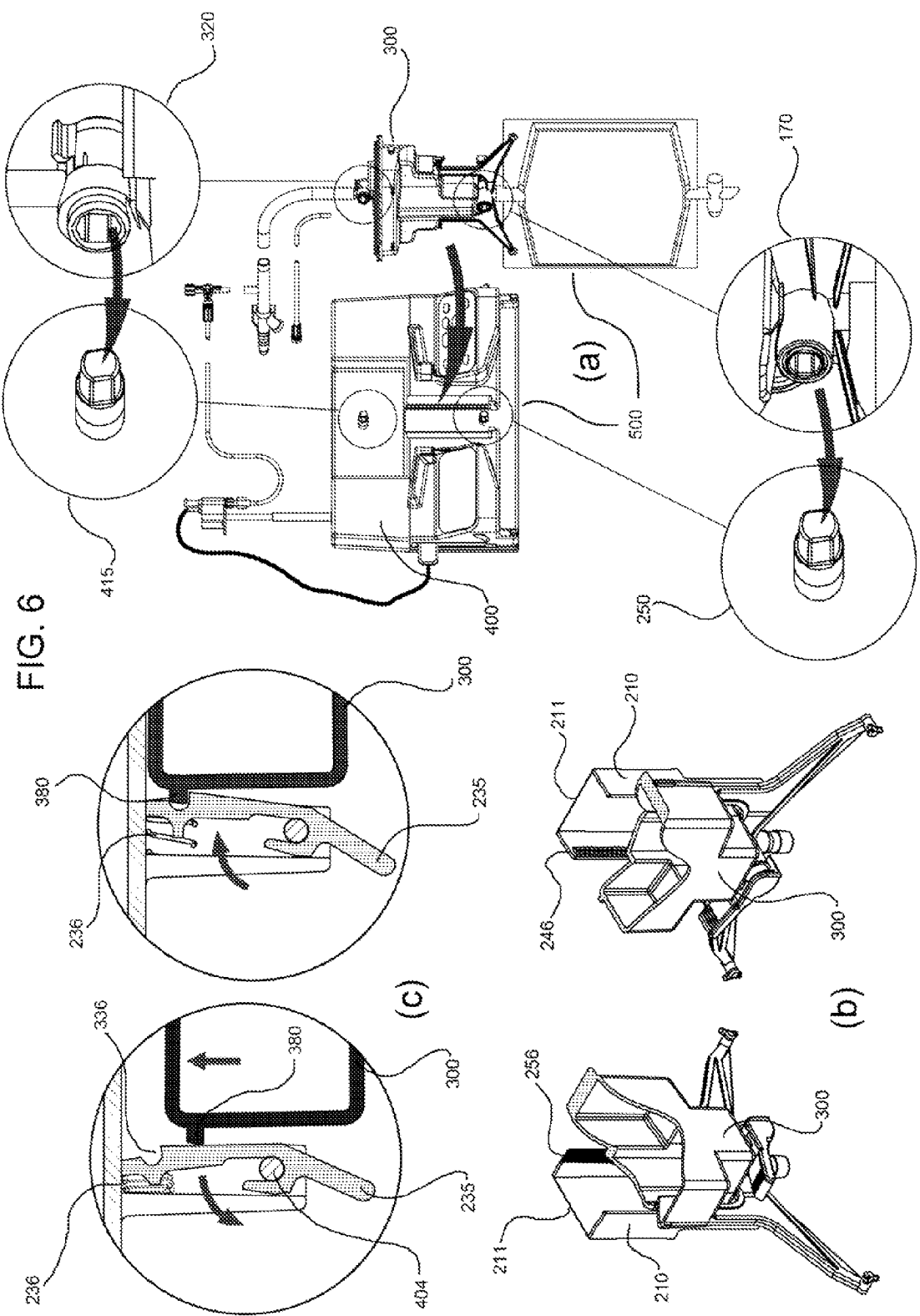
FIGS. 6(a) to (c) show schematically how a disposable container is engaged with an electronic unit of a FSPM apparatus according to the present invention.

FIG. 6 shows all engagement elements of the disposable container 300 regarding the electronic unit 400 composing a part of the FSPM 500. FIG. 6 shows the assembly of the double motor FSPM unit 500, which is composed of the disposable vessel 300 engaged in to the electronic double valve unit 400. In FIG. 6(a) the disposable unit 300 can be seen from its back side, before engaging into the electronic unit 400. In the two details of this figure, the upper & the lower shafts 415 & 250, respectfully, of electronic unit 400 and inlet & outlet valve 320 & 170, respectfully, of disposable container 300 valves 320 & 170 can be seen before engaging. A detailed explanation will follow regarding FIG. 7. In addition to the valves and shafts engagement, there can also be seen in FIG. 6(b) an enlarged view illustrating the main elements of the optical segment 210 and their specific relative positioning with respect to the of the disposable container 300. Container 300 is fully engaged into optical cavity 211 of the electronic unit 400, as shown from two different sides the container 300 and photo detector strip 256 and led array 246 of optical segment 210.

FIG. 6(c) shows the engagement of the disposable container 300 with its side notches or projections 380 with the electronic unit 400 by means of clamps 235. This is shown in two steps, initiation stage and engagement step. Initially clamp 235 pivots counter clockwise on axis 404 as vessel 300 is pressed into place. In the engagement step, clamp 235 pivoting clockwise on axis 404 due to spring pressure 236. In this position notch or projection 380 stays in cavity or slot 336 until release of vessel 330 by manually turning clamp counter-clockwise. This clamping feature or functionality is relevant to all containers within the scope of the application.

FIG. 7 shows views partly in section of the inlet and outlet valves in their open and closed positions and shows the shafts engagement. FIG. 7(a) and FIG. 7(b) show the inlet and outlet valves, respectively, and includes partial sectional views of the collection vessel 600 and 300, respectively. The outlet valve 170 in FIG. 7(b) has an overflow feature to allow passage of liquid during vessel overflow, regardless of being open or closed. This overflow feature pertains to the outlet valve exclusively. The valves are both of stopcock-like valves where one end of the valve shaft is fitted with a handle and the other end of the valve shaft is designed to engage the output drive of the motor that can automatically rotate the valve between its open and closed positions responsive to the motor drive signals.

When the outlet valve 170 is in open position, it creates an alignment between orifice 663 and the drainage hole 173 to allow fluid passage from vessel to outlet connector 640. In addition the open position seals the overflow passageway 172 from the outlet connector 640. When the outlet valve 170 is in closed position, it seals the orifice 663 from the drainage hole 173 and creates an overlap between the overflow passageway 172 and outlet connector 640 to allow overflow liquid to pass from overflow channel 667 via orifice 668 to the overflow passageway 172 and out from outlet connector 640. As noted above, flow out of the collecting vessel is controlled by the outlet valve 170, which is driven by a suitable electro-mechanical driver 250' (shown in FIG. 3) via a drive shaft engagement segment 250 with a protrusion 251. The protrusion 251 has a non-circular periphery and fits into the geometrically corresponding cavity 171 inside the outlet valve 170. Outlet valve 170 can also be opened or closed manually by lever 174. Outlet valve 170 is depicted with vessel 600, as an example; all said features for the outlet valve 170 pertain to all other vessels 600, 1000, 300, 3000 as well.

The inlet valve 320 of FIG. 7(a) controls the flow into the collection vessel 300. Unlike the outlet valve 170, the inlet valve 320 has no overflow compensation and only maintains two positions, opened to allow flow into vessel from inlet connector 352 via drainage hole 322 and into vessel and closed to inhibit said flow. The open and closed position of inlet valve 320 can be controlled by the electro-mechanical driver 415' (shown in FIG. 3) or by a manual lever 323. Motion transmission from the electro-mechanical driver 415' is achieved via the drive shaft engagement segment 415 with a protrusion 416. The protrusion 416 fits into a geometrically corresponding cavity 321 inside inlet valve 320. Inlet valve 320 is depicted with vessel 300 as an example; all said features for the inlet valve 320 pertain to vessel 3000 as well.

Figure 8:
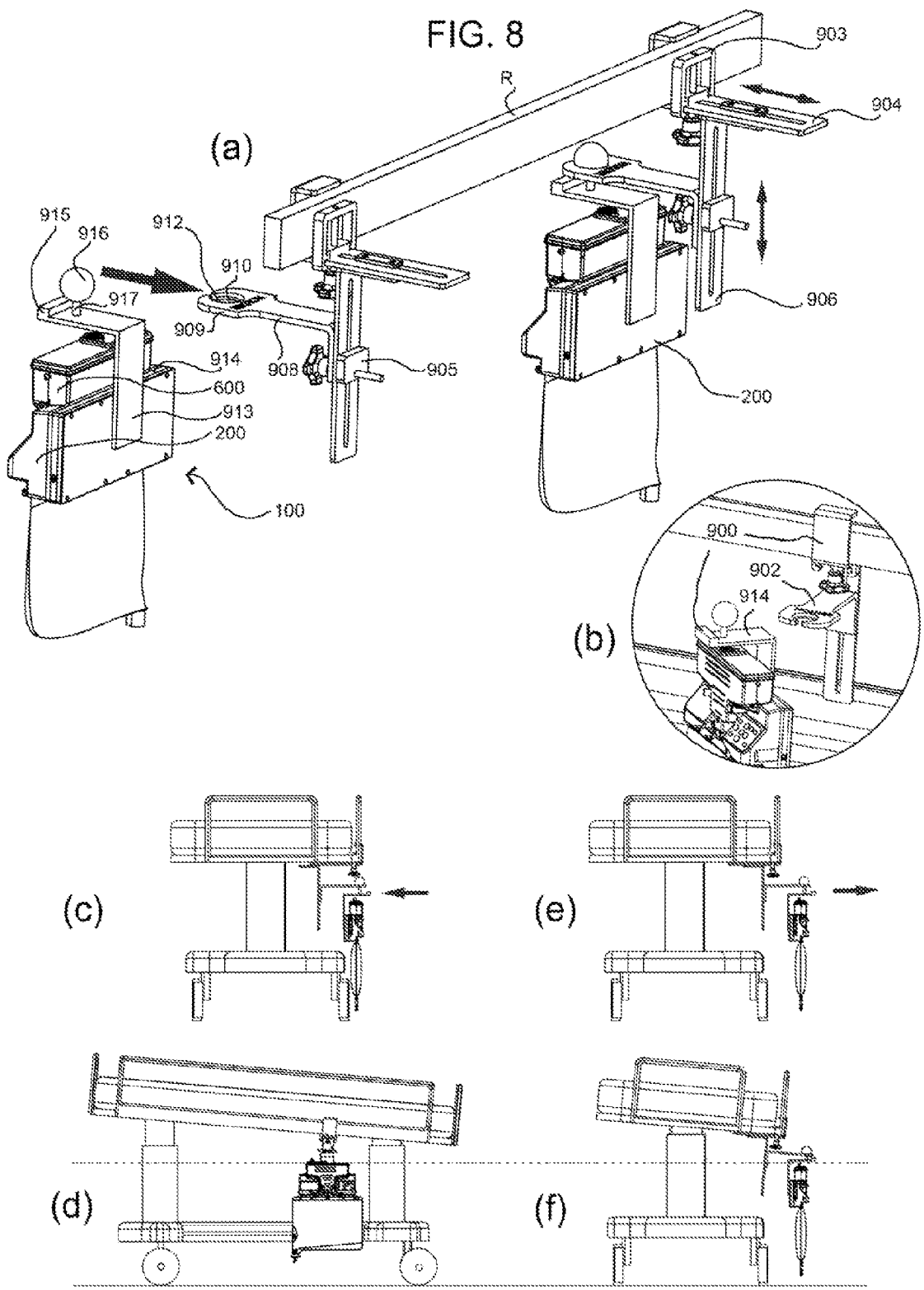
FIGS. 8(a) to (f) show schematically how a Fluid Secretion Pressure Monitor (FSPM) apparatus is hung on a bed, and also on a hospital pole as seen in FIG. 5.

FIG. 8 depicts the hanging mechanism of the FSPM and illustrates how the mounting apparatus 900 and the way the FSPM unit 100 is engaged or disengaged with the mounting assembly 902. Apparatus 900 consists of two sub units, the L-shape member 914 and the assembly 902 which consists of 4 units 903,904,906,908. The member 904 is clamped to the bed rail R by lockdown of sliding flange 903. Member 906 is L-shaped and its short leg is held by the member 904 such to allow 906 to slide relative to 904 in the grooved direction. Member 908 is L-shaped and its short leg is held by the member 906 by a conventional pin and slot arrangement 905 as depicted in FIG. 8(a) to allow 908 vertical movements with respect to 906. The long leg of member 908 terminates in an enlargement 909 that defines a circular through bore 910 that has a notched opening 912 along its long axis. Thus the bracket 902 can be adjusted in three dimensions relative to R, the horizontal plane and vertically.

Another L-shape member 914 has one leg 913 fixed to the back of electronic unit 200 of the FSPM unit 100 with the other leg 915 extending over the top of the collection vessel 600, a cubic shaped counter balance weight is located at the extended end of 915 to counter the weight of FSPM unit 100. The free end of leg 915 has a projection 916 in the shape of a sphere having a greater diameter than the bore 910 mounted on a short stub 917 that has a diameter less than the opening 912. Stub 917 holds the sphere or ball 916 spaced above leg 915. The FSPM unit 100 is mounted on the bracket 902 by sliding the rod or stub 917 through the opening 912 and seating the ball 916 in the through bore 910. This mounting assembly maintains the FSPM unit 100 in its horizontal leveled position. The spherical joint 916 is a gravity centering joint which maintains the FSPM unit 100 aligned with gravity regardless of the bed tilt. The engagement of the FSPM unit 100 on the bracket 902 is shown from another angle in FIG. 8(b) the anti-tilt effect is shown more graphically in FIGS. 8(c) to 8(f). The same anti-tilt hanging is used when hanging the system on a hospital pole in order to avoid tilting when pole is moving as seen in FIG. 5 and in FIGS. 8(c) to 8(f) where the automatic adjustment due to gravity is shown in front view and side view. FIGS. 8(c) and 8(e) show the bed 700 positioned horizontally and FIGS. 8(d) and 8(f) show the bed 700 positioned with a tilt. The FSPM unit 100 remains horizontal despite the bed tilt since the ball 916 acts as a spherical joint in bore 910, causing gravitational alignment.

FIGS. 8(c) and 8(f) give additional illustration of the adjustability of Member 906 relative to member 904 to allow retraction under the bed line.

Figure 9:
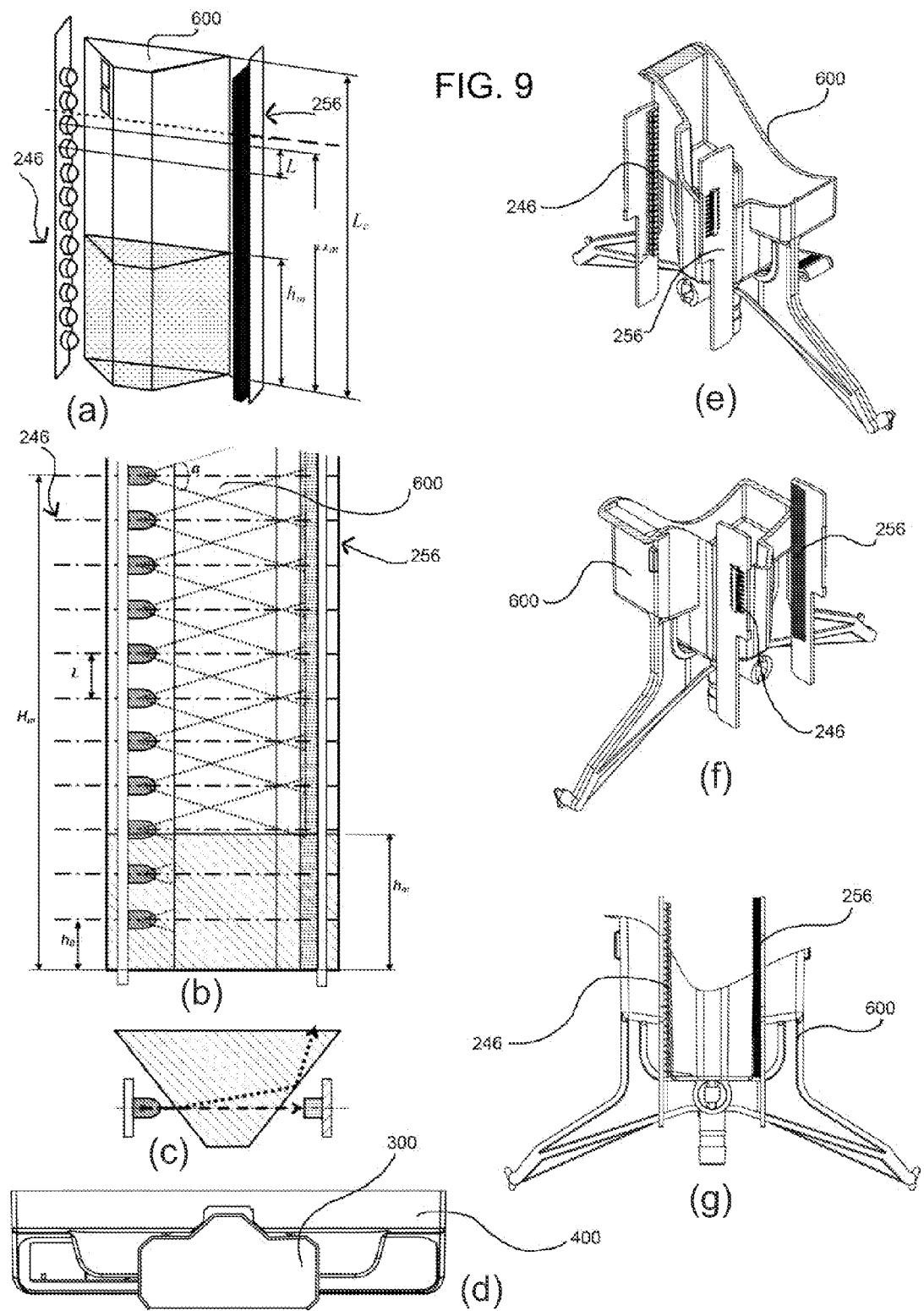
FIGS. 9(a) to (g) are schematic views illustrating emission across the optical gap of the Electronic unit and how the determination of liquid level is made and also show schematically details of the optical unit of the present invention.

Referring to FIGS. 9 to 11, the measuring of the liquid's surface height $h_m$ is accomplished by scanning the space of the optical segment 210 of the transparent measuring vessel 600, 1000 or 300,3000 that is placed between vertically oriented light emitter diodes (LED) array 246 and an elongated photodetector 256. This scanning is based on the refraction of the emitters' rays on the boundary of two media due to the special measuring vessel's construction. FIG. 10 illustrates various vessel configurations and shows how light is refracted in dependence on whether there is liquid present in the light path as it traverses the vessel. Three vessel shapes are shown and the effect of light refraction is depicted for each. LEDs 247 are used for vessel identification as will be explained hereinafter.

FIGS. 9 to 13 show the scanning in more detail and show how it is controlled and processed by the electronic unit 200 that contains optical cavity 211, in which the optical segment 210, composed of array 246 and elongated photo detector 256, is vertically positioned and mounted. The optical segment's height extends the entire vessel's optical part's height and the light emitted by the LEDs is transmitted through the measuring vessel optical part. The electronic unit 200 is designed, under the control of MCU 740, to continuously and serially and cyclically light the LEDs for a defined interval from bottom to top, to detect the intensity or luminance of detected light by the photodetector 256 for each LED in succession and to output signals correlated to the detected intensity or luminance, which are stored in memory. These output signals are processed by MCU 740 to determine the height of the collected liquid column as will be explained in detail in the following.

As seen in FIGS. 9 to 12 the liquid column height $H_m$ inside the optical part is smaller than the electronic unit's optical cavity height $L_c$. The array column 246 has n light emitters designed to emit a diverging light of specified viewing angle $\alpha$. The measuring height $H_m$ contains (n−1) distances (L) between neighboring emitters' optical axis: $H_m$=(n−1) L. The geometrical parameters of the measuring vessel's optical part provide the desired degree of emitter rays' refraction. FIGS. 9 to 12 show, respectively, vertical and horizontal cross sections of the optical part. Thus, the output signal level of the photodetector 256, enables measuring the height of liquid column. To provide a continuous measurement scale independent of the emitters' positions, the LED array 246 is constructed such that every emitter's diverging ray partially overlaps the rays of the neighbor emitters, see FIGS. 9 to 12 showing a vertical cross section of optical segment, where:

$1_i$ and $1_{i-1}$—neighbor emitters of emitters' array 246;
$EOA_i$ and $EOA_{(i-1)}$—neighbor emitters' optical axis;
W—distance between the emitters' array and the photodetector;
$h_{ol}$—overlap.

The value of overlap is defined by the above-mentioned geometric parameters of the optical system.

$$h_{ol} = 2W \cdot \tan\left(\frac{\alpha}{2}\right) - L \tag{1}$$

Thus, varying W, L and/or $\alpha$, can achieve the required value of overlap.

The algorithm, set forth below, for processing measurement results for the signals of the photodetector, illuminated sequentially by neighboring emitters, is based on the argument that in the case of 50% photo detector's luminance, the liquid's surface level either coincides with the optical axis of the corresponding emitter. In this case the liquid's surface level is calculated by using the following expression:

$$h_m = h_0 + nL \tag{2}$$

Where:
hm—liquid's surface height;
$h_0$—height of lowest emitter's optical axis;
n—emitter's number (in this case n=i−1).

If the liquid's surface level is between two neighbor emitters (FIG. 32c and FIG. 33) so the $h_m$ is determinable from two values of the photodetector's output signal; see FIG. 11 showing a graph of the photodetector's illuminance vs. detector.

$$h_m \approx h_0 + nL + \frac{\gamma_i + \gamma_{max} - 2 \cdot \gamma_{(i-1)}}{(\gamma_i + \gamma_{max}) \cdot \frac{L}{W_{es}} - \gamma_{(i-1)}} \cdot L \quad (3)$$

Where:
$h_m$—height of the liquid surface relative to the bottom of the measuring vessel;
n—The emitter's number shaded by the liquid more then to 50%;
L—distance between neighbor emitters' optical axis;
$h_0$—height of the $1^{st}$ emitter's optical axis.
$\gamma_i$, $\gamma_{(i-1)}$—photo detector's illuminance caused with emitters number: n=i and n=i−1;
$W_{es}$—distance from the emitter to the measuring vessel in a longitudinal cross section.

A tilt sensor may be used to determine the vertical orientation of the collecting vessel 600. Alternatively, the assembly can be mounted on an anti-tilt device as explained herein. Also, averaging the photodetector's signals significantly reduces the influence of the irregular and periodic fluctuations of photo signals. This influence reduction is caused both, by optical and/or mechanical causes, and also by electromagnetic interference. The averaging of the signals is carried out in three steps:

1. multiple scanning with simultaneous recording of the results in the temporary memory;
2. analysis of the recorded results and the removing of the "artifacts", i.e. results differing significantly from the others;
3. averaging and storing of the remaining results for data processing.

Thus in data processing, after above mentioned steps, only "cleaned" and averaged results are used.

To compensate the impact of external lighting, the measuring vessel's scanning order is organized as follows:

a. measuring the signal with the non-activated emitters ($\gamma_{NAE}$), while averaging the signal and recording the result in the temporary memory;

b. generating an output analog signal, using the internal DAC, which is equal to the temporary stored value: $\gamma_{REF} = \gamma_{NAE}$, and feeding it to the negative input of the measuring differential ADC;

c. measuring the difference of the signal $\gamma_{AE}$ when the emitter is activated and feeding this result to the positive input of differential ADC, and the signal to the negative input: $\gamma_i = \gamma_{AE} - \gamma_{NAE}$;

d. storing the result $\gamma_i$ in the memory as the tasked signal's value.

Thus, the value stored in memory ($\gamma_i$) does not contain an external light component ($\gamma_{NAE}$). Implementation via the multiprocessor of the system of the above-described sequence for each measurement of the photodetector's signal, given the high-speed of the measurements, allows for a high level of compensation on the influence of external illumination on the measurement results.

Increasing the number of mutually overlapping emitters (by reducing the distance between their optical axes and/or increasing the emitter's viewing angle) significantly improves the resolution and accuracy of measurement when using a more detailed calculating algorithm.

Scanning results that are stored in memory perform the tabulated function of illuminance from the emitter's number:

$$\gamma_i = F(i), \text{ where } 0 \leq i \leq n \quad (4)$$

This function is the source of DATA for calculation via the computer of the system of the liquid level height. In order to find $h_m$, any interpolation method, say Lagrange Polynomial Interpolation can be used. For the interpolation, it is reasonable to use only a few points that can provide concrete information about the value of $h_m$. According to the Lagrange Polynomial Interpolation, the function $\gamma = F(h_m)$ can be written for any virtual emitter placed so that its optical axis height is equal to liquid's level $h_m$. In this case, the photodetector's signal caused by this emitter is equal to half of the maximal possible signal:

$$\frac{1}{2} \gamma_{max} = \sum_{j=n_b}^{n_t} \left[ \gamma_i \cdot \frac{\prod_{j=n_b, j \neq i}^{n_t} (h_m - h_0 - j \cdot L)}{h_m^{(n_t - n_b - 1)} \cdot \prod_{j=n_b, j \neq i}^{n_t} (i - j)} \right] \quad (5)$$

Where:
$h_m$—height of the liquid surface relative to the bottom of the measuring vessel;
$n_t$—the number of the top emitter used for interpolation;
$n_b$—the number of the bottom emitter used for interpolation;
L—distance between neighbor emitters' optical axis;
$h_0$—height of the 0-emitter's optical axis;
$\gamma_i$—photo detector's illuminance caused with the i-emitter ($n_b \geq i \geq n_t$);

After the height is found, the tabulated function $v_i = F(h_i)$ is used to calculate the liquid volume $v_m$. To calculate $v_m$, the above mentioned interpolation method is used again:

$$v_m = \sum_{j=n_b}^{n_t} \left[ v_i \cdot \frac{\prod_{j=n_b, j \neq i}^{n_t} (h_m - h_0 - j \cdot L)}{h_m^{(n_t - n_b - 1)} \cdot \prod_{j=n_b, j \neq i}^{n_t} (i - j)} \right] \quad (6)$$

Where:
$v_m$—desired value of liquid volume in the measuring vessel;
$v_i$—value of liquid volume corresponding height of the i-emitter's optical axis, defined with function $v_i = F(h_i)$, that is specific for every type of vessel.

For deviation from the horizontal corrections, if necessary, the invention uses a two horizontal coordinates' tilt-sensor, which provides the measuring of the horizontal deviation values for correction of the volume measurement.

$$v_{mnh} = F_d(v_m, \delta_x, \delta_z) \quad (7)$$

Where:
$v_{mnh}$—measured value of liquid's volume at any horizontality deviation;
$v_m$—measured value of liquid's volume without horizontal deviation;
$\delta_x$, $\delta_z$—horizontal deviation's angle in two optical system's coordinates' axis.

FIGS. 12(a) to (f) show a novel identification device and technique for automatically determining the type of vessel connected to the electronic unit 200 and/or the optional double motor electronic unit 400. As shown the identification approach for the type of vessel connected to the electronic unit 200 and/or the optional double motor electronic unit 400 reads the light intensity received from the two upper emitters or vessel type identifiers 247 and compares their individual values against the known minimal light intensity value indicating unobstructed passage of light through the vessel walls. By placing opaque tabs 696 on the vessel wall at the precise location where the two said vessel type identifiers 247 are located, which effectively prevents the light emanating from them from reaching the elongated optical photodetector 256, four different types of collecting vessels can be recognized. This can be clearly visualized on FIG. 12, where by covering or not the beams emanating from the two vessel type identifiers 247, according to the four possible combinations shown, four different photodetector's 256 reading are obtained. These readings are then compared against known ones identifying each particular vessel type. As a result of this, during regular operation the liquid level is not permitted to reach the vessel type identifiers 247.

The operation of the FSPM unit 100 automatically is as follows. The valve 170 is closed and bio-fluid is allowed to drain into vessel 600 for predetermined or preselected time intervals. The volume is periodically measured by calculating as previously described, recorded and saved to memory. At the end of a time interval, valve 170 is opened and the bio-fluid is drained into the secondary reservoir 580, which is drained or replaced when full. At the same time the volume of the vessel is monitored and if the volume reaches a preset level before the time interval has elapsed, this volume is recorded and saved to memory and valve 170 is opened to drain vessel 600. Volume is calculated as previously described. Data regarding the volume and time can be displayed on display 260. Alternatively, a graph can be plotted showing volume vs. time and shown on display 260 and saved to memory. Also, the apparatus can be monitored and operated manually by a nurse and emptied manually by the nurse manipulating valve 170 to open to drain and close to collect bio-fluid and recording the volume and time.

The overall operation of the Double motor FSPM unit 400 automatically is as follows. The double motor FSPM unit 400 is first placed besides the patient at a convenient height where the DPT 520 can be raised or lowered to the level of the organ to be drained by means of the extendable tube 550. After the double motor FSPM unit 500 is in place, the DPT line 530 is primed with saline through the priming port 510 while the stopcock 540 is at the open position. After the DPT cable 560 has being connected to the double motor Electronic Unit 400, and the high flow high flow drainage tube 570 is connected to the patient, the unit can be powered on and the patient's bio-fluids drainage and measurement can be initialized.

The double motor FSPM unit 400 is programmed to record and evaluate the physical values of fluid pressure and volume vs. time in order to determine the particular intra-abdominal pressure of the patient at all times. This is achieved by use of a double valve approach, where each valve 320 and 170 is attached to one of the servo motors of the double motor Electronic Unit 400, and the valves are controlled by software commands in accordance to the specifications of the end users.

The different evaluative options of the double motor FSPM unit 400 are as follow: to record and evaluate volume and pressure at set intervals of time and/or to record and evaluate volume and time at peak intervals of intra-abdominal pressure. In order to evaluate volume and pressure at set intervals of time, the double motor FSPM unit 400 opens the upper inlet valve 320 and begins draining the bio-fluids from the patient, while keeping the outlet valve 170 closed. As the bio-fluids are being drained, the double motor Electronic Unit 400 records and displays the pressure inputs from the DPT 520 and the volume level inside the collecting vessel 300 at predetermined or preselected time intervals. The volume level inside the collecting vessel 300 is measured by the vertically oriented array of LED's serially and cyclically emitting light through the LED slit that is detected by the vertically oriented photodetector via juxtaposed slit 255. The sensed and detected light is processed in the MCU, in the manner described previously in order to determine the level of the bio-fluids inside the said double valve collecting vessel 300. The system is programmed so that the measured level is plotted against time, recorded and displayed to show volume accumulation of the bio-fluids. After a predetermined or preselected time, the level in vessel 300 is measured and valve 170 is turned from closed to open and the fluid is drained from the collection vessel 300 to the secondary reservoir 580. By the same token, if the level that is constantly being monitored reaches a predetermined or preselected level before the time interval has elapsed, valve 170 is turned to open and fluid is drained from the collecting vessel 300. These functions are recorded and saved in memory and processed by the MCU and displayed appropriately on the display 260 of electronic unit 400. Also, the DPT 520 continually detects and monitors the pressure in the cavity or organ being monitored and this is plotted against time and liquid volume see FIG. 14. The electronic unit 400 is programmed to monitor the pressure in the cavity or organ of the patient being monitored by frequently cycling valve 320, and to close valve 320 periodically at set time intervals or whenever the monitored cavity pressure reaches a preset maximum value, whereupon the valve 170 is opened to drain the vessel 300 see the plot of FIG. 15. The operation of the unit can be manually controlled by a nurse checking the status of liquid volume and cavity pressure and manipulating valves 320 and 170 at appropriate times, while recording the pressure, volume and time.

Figure 12:
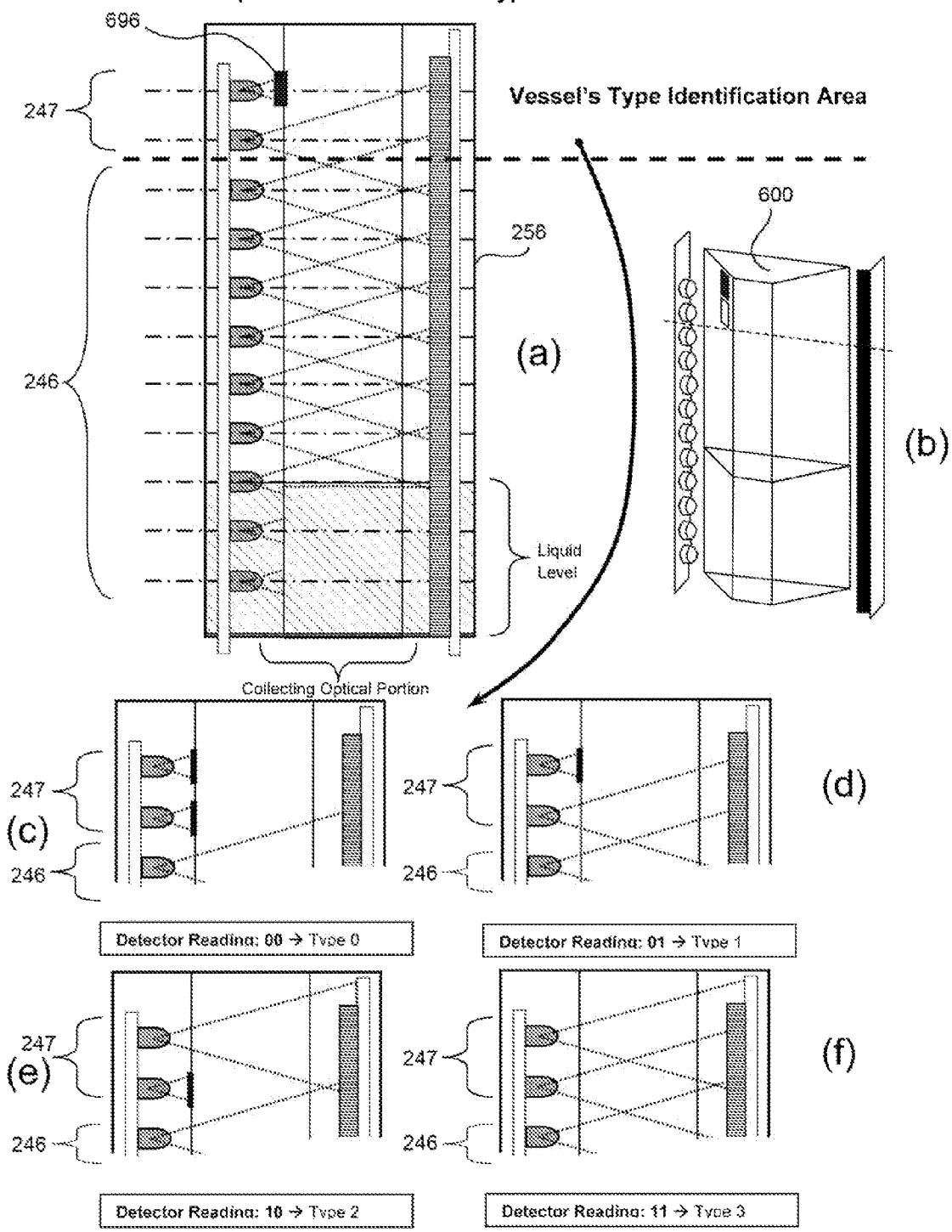
FIGS. 12(a) to (f) are schematic views illustrating determination of the type of vessel mounted on the Electronic unit
Figure 13:
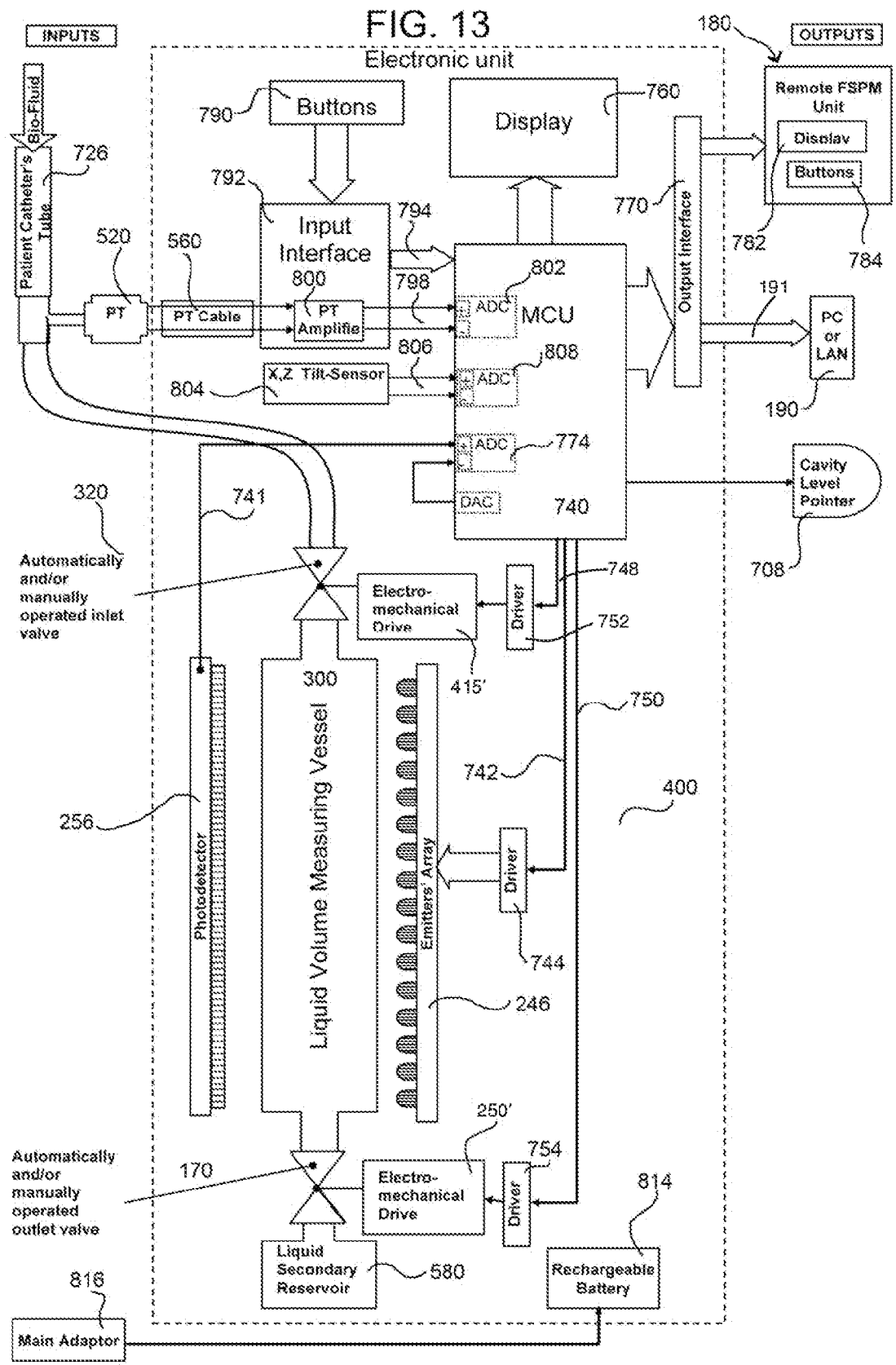
FIG. 13 is a block diagram of the inventive apparatus, 2-VALVE FSPM, showing details of the electronic components and their interaction.
Figure 14:
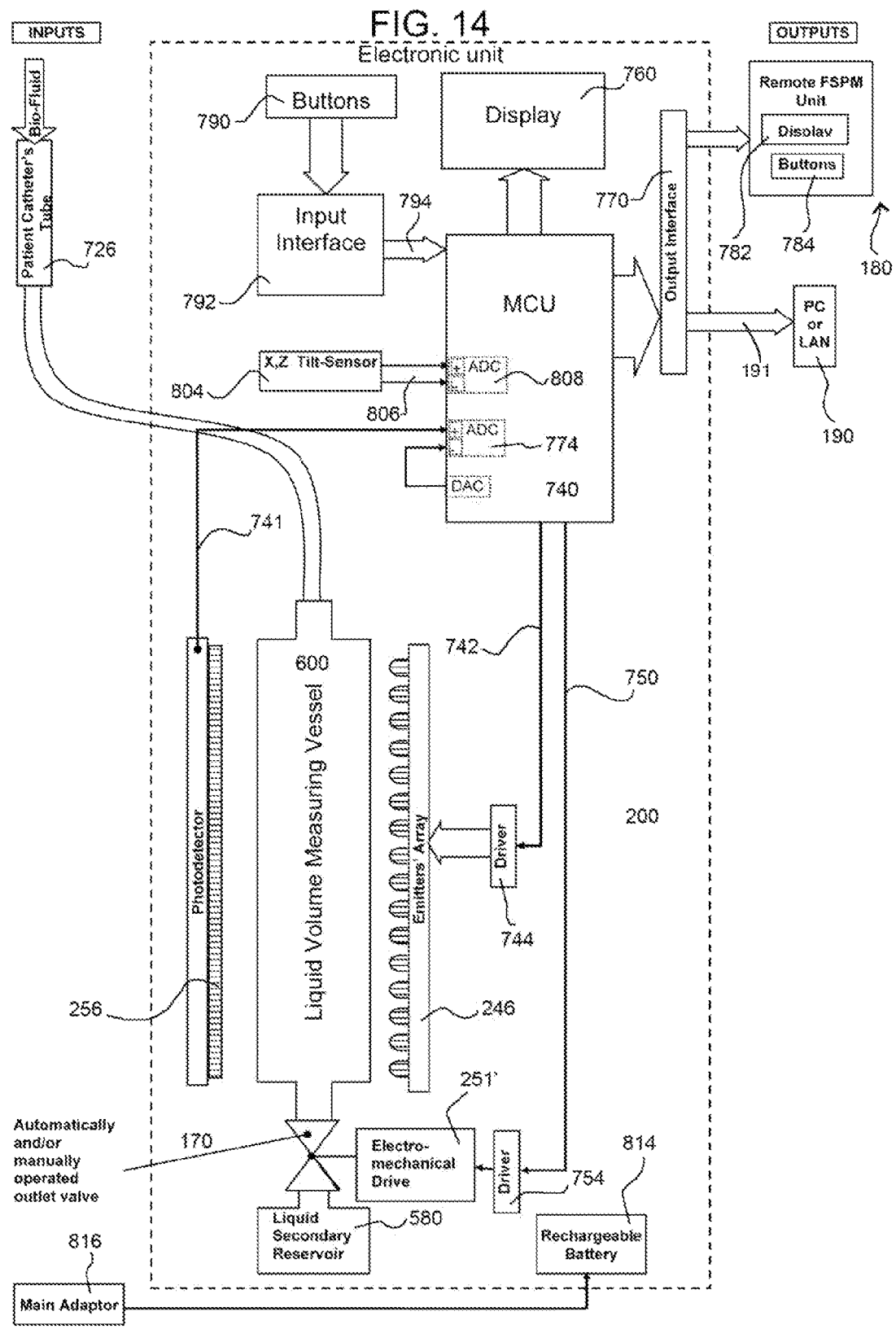
FIG. 14 is a block diagram of the inventive apparatus, 1-VALVE FSPM, showing details of the electronic components and their interaction FIGS. 15(a) and (b) show graphs illustrating pressure release schemes for the inventive apparatus.

FIGS. 9 and 11 are schematic views illustrating emission across the optical gap and the determination of liquid level. FIG. 10 shows various vessel configurations. FIGS. 12(*a*) to (*f*) are schematic views illustrating the process of determining the type of vessel mounted on the electronic unit. FIG. 13 is a block diagram of the inventive apparatus showing details of the electronic components for a double valve FSPM unit and their interaction. FIG. 14 is a block diagram showing the components for a single valve FSPM unit and their interaction.

FIG. 13 illustrates schematically a block diagram of the measuring components and the electronic components of the FSPM double valve unit. The simplified block diagram is shown in FIG. 14, which illustrates the 1-valve FSPM unit. The double valve FSPM unit is shown in FIG. 13 within the dotted lines and consists of an automatically and/or manually operated inlet valve 320 leading from a disposable pressure transducer 520. The inlet to the pressure transducer is the patient's catheter tube 726 originating from a cavity of the patient, such as the patient's bladder and carrying bio-fluids. Valved inlet 320 introduces the patient's bio-fluids into a double valved liquid measuring vessel. Liquid is drained from vessel via an automatically and/or manually operated outlet valve 170 and passed to a secondary liquid reservoir. Liquid level is measured in vessel 300 by a vertical array of LEDs 246 coacting with a vertically oriented photodetector strip 256 connected via line 741 to ADC 774. The LEDs-Array 246 are powered and controlled by MCU 740 via line 742 and driver circuit 744. Valved inlet and outlet 320 and 170 are operated by conventional electromechanical drives 250' and 415', which in turn are powered and controlled by MCU 740 via lines 748, 750 and drivers 752, 754. MCU 740 outputs to a display 760 and to an output interface 770, which in turn can send its signals to a remote control FSPM unit 180 having a display 782 and control buttons 784 for a manual operator to input, output, and program or control. Output interface 770 can also be coupled to a PC or LAN 783 and is coupled to a cavity level pointer 785. Buttons 790 are connected to input, output, and program or control the MCU 740 via an input interface 792, which is coupled to the MCU 740 via serial bus 794.

The disposable pressure transducer 520 generates an output of pressure and transmits its output signal via DPT cable 560 to the input interface 792 where it is processed in amplifier 800 and transmitted via lines 798 to ADC 802 connected to the MCU 740 where the signals are processed. An X, Z tilt-sensor 804 generates tilt signals and transmits them via lines 806 to ADC 808 connected to the MCU 740 where the signals are processed. The output of the photodetector strip 736 outputs a luminance signal via line 810 to MCU 740 where it is processed. A rechargeable battery 814 is included as the power source for all components of the FSPM double valve unit and is connectable to mains or AC power source 816 for recharging. It will be appreciated that in the above description both inlet valve and outlet valve are included. Thus, the block diagram, with appropriate adjustment, can be used for both the double valve & single valve FSPM units. The connections, coactions and components for the single valve FSPM are shown in block diagram in FIG. 14.

Referring again to FIGS. 9 to 11, the measuring of the liquid's surface height $h_m$ is accomplished by scanning the space of the optical segment 210 of the transparent measuring vessel 600, 1000 or 300, 3000 that is placed between vertically oriented light emitter diodes (LED) array 246 and an elongated photodetector 256. This scanning is based on the refraction of the emitters' rays on the boundary of two media due to the special measuring vessel's construction. FIG. 10 illustrates various vessel configurations and shows how light is refracted in dependence on whether there is liquid present in the light path as it traverses the vessel. Three vessel shapes are shown and the effect of light refraction is depicted for each. LEDs 247 are used for vessel identification as explained herein.

FIGS. 15(a) and 15(b) show pressure release schemes. The parameters for these schemes are $P_{max}$: Predetermined threshold pressure for opening of Inlet Valve; Drained Volume: the recorded volume of the liquid collected in the vessel after the inlet valve opening; Inlet Valve State: can be either closed or open denoted 0 or 1, respectively; and Outlet Valve State: can be either closed or open denoted 0 or 1, respectively.

FIG. 15(a) depicts graphically the dependencies of pressure, volume, inlet valve and outlet valve for a pressure controlled release scheme. The pressure is measured in the fluid line from the inlet valve to the patient and is compared to a threshold value $P_{max}$. Upon crossing the threshold value, the outlet valve is open briefly to empty the vessel and then closed. After outlet valve has closed the inlet valve is opened briefly to allow the release of pressure from the patient by releasing fluid into the vessel. The new volume of said fluid in vessel is measured and denoted as "Drained Volume". In this figure it can be seen that there is a pressure rise in the drained cavity, while there is decreasing in the fluid output, this can be indicative of an intra-abdominal pressure rise.

FIG. 15(b) depicts graphically the dependencies of pressure, volume, inlet valve and outlet valve for a time controlled release scheme. The difference from the pressure controlled release scheme is that in addition to the release by crossing pressure threshold value $P_{max}$ (arrow) the pressure is released periodically wherein period is defined by user. In this figure the period is 10 min. as with the pressure controlled release scheme, prior to pressure release the outlet valve is opened briefly and then closed followed by opening of the inlet valve. Subsequently fluid passes from the patient to the vessel, the pressure drops, the inlet valve is closed and the Drained Volume is measured. In this figure if the drained cavity is the bladder although there is no raise in pressure there is lowering of the urine output that can be due to different clinical situations, not related to rise in intra-abdominal pressure.

FIG. 16 depicts graphically the dependencies of pressure, volume, inlet valve and outlet valve for an induced pressure scheme. Inlet and outlet Valve State: can be either closed or open denoted 0 or 1, respectively; occasionally there is a need to induce pressure within the patient. When this mode is selected both valves open briefly to zero the system and closed again a known amount of Saline (e.g. 50 ml) is injected into the patient from the line connecting inlet valve to patient, pressure builds up, is measured and released according to one or more predefined triggers (i.e. steady pressure, threshold reached, manual release and timer). The release of pressure is done by opening the inlet valve after which the amount of volume (e.g. 10 ml) is registered by deducting the amount injected into patient (e.g. 50 ml) from the volume in vessel (e.g. 60 ml). After pressure has been released by opening of the inlet valve the system reverts to its previous monitoring and pressure release scheme. The schematic of induced pressure is also described in FIG. 21b.

Figure 17:
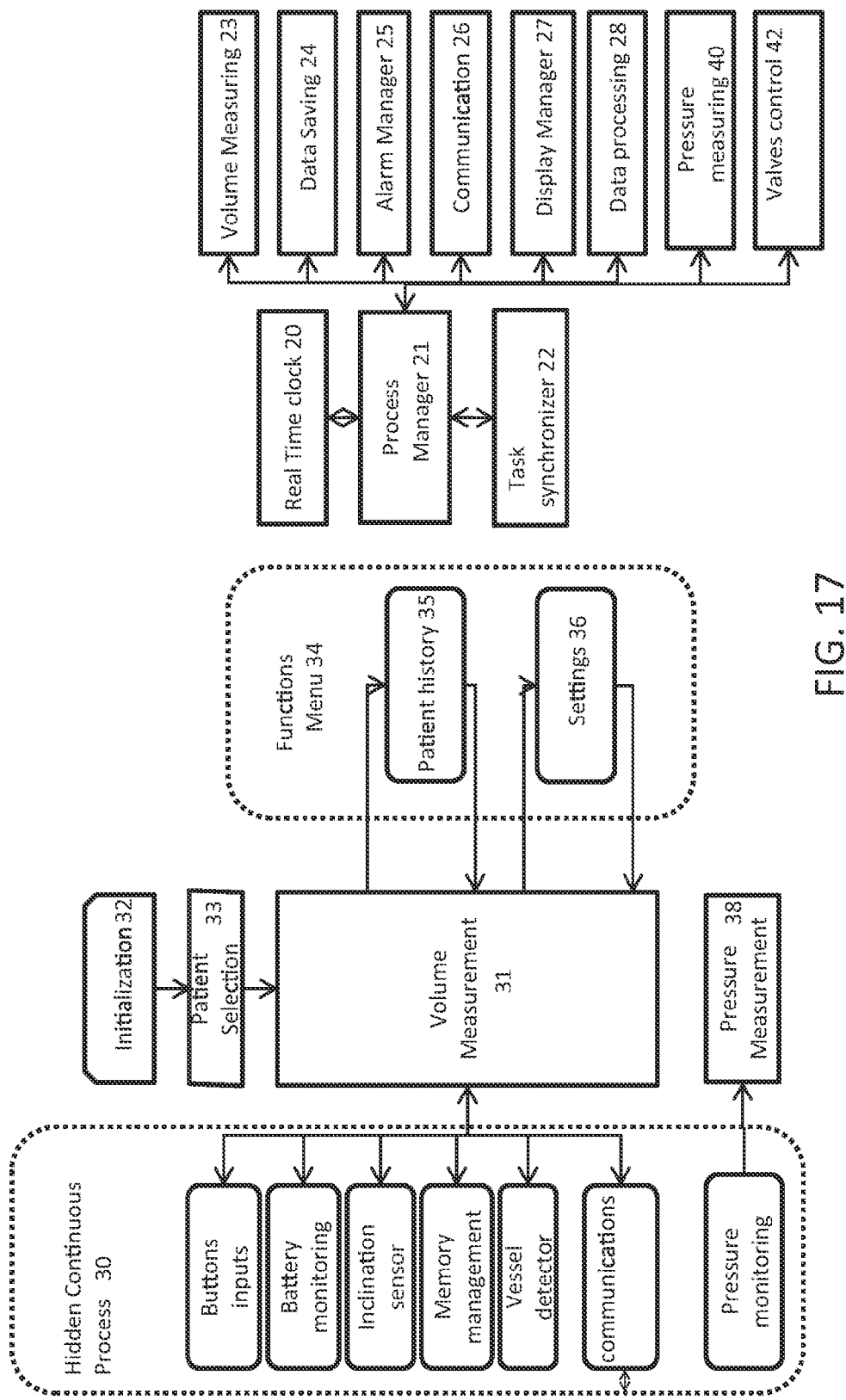
FIG. 17 is a block diagram showing the software main modules of the inventive apparatus.

FIG. 17 depicts, in block form, the software main modules wherein a real time clock 20 connected to process manager block 21 which is also connected to task synchronizer block 22. The process manager 21 controls the volume measuring block 23, data saving block 24, alarm manager 25, communication block 26, display manager 27, data processing block 28, pressure measuring 40 and valves control 42. The main process and functions are also shown in FIG. 17 and consist of hidden continuous processes 30 including button inputs, battery monitoring, inclination sensor, memory management, vessel detector, communications and pressure monitoring. The communications process relays data internal and external to process 30. Process 30 feeds volume measurement block 31 that is controlled by initialization 32 and patient selection 33. Block 31 interacts with functions menu 34 that includes patient history 35 and settings 36. Warnings and alarms are provided depending on device mode and events. Volume measurement 31 reacts responsive to events including vessel not in cradle, valve is jammed, sensors not showing vessel properly, battery problem, contents of memory reaching limit and communication problem detected. The responsive warning or alarm is set forth in detail in FIG. 18

FIG. 18 shows, in block form, the software Warnings and alarms. The various scenarios for an event mode, (possible reason) and the consequential display are as follows:

Device Mode:

Volume measurement 31:

Event: Vessel is not in the cradle or sensors do not show vessel when they should (vessel removed or misplaced). In this event the display will show "Insert URX".

Event: calibration fails: (dirty vessel). Display: "Insert URX"

Event: the valve is jammed or not in position (valve is not rotating as commanded).

Display: "check URX"

Event: the valve is jammed or not in position (the valve has been rotated manually).

Display: "check Valve"

Event: too much environmental light (direct sunlight). Display: "Too much light"

Event: device inclined (bed inclined greater then compostable). Display: "Straight device".

Pressure Measurement 38:

Event: pressure level out of limits (measured cavity over pressurized or DPT reading out of scale). Display: "Pressure alarm"+buzzer+red light.

Event: pressure level out of limits (inlet valve is open, NO pressure drop). Display: "Check DPT".

General:

Event: battery voltage reaches limit (20% to 10%). Display: Low battery icon.

Event: battery voltage reaches limit (10% to 5%). Display: "Low Battery".

Event: battery voltage reaches limit (5% to 1%). Action: automatic shutdown.

Event: memory is reaching the limit. Display: "Low memory"

Event: communications problem. Display: "Communication problem"

Figure 19:
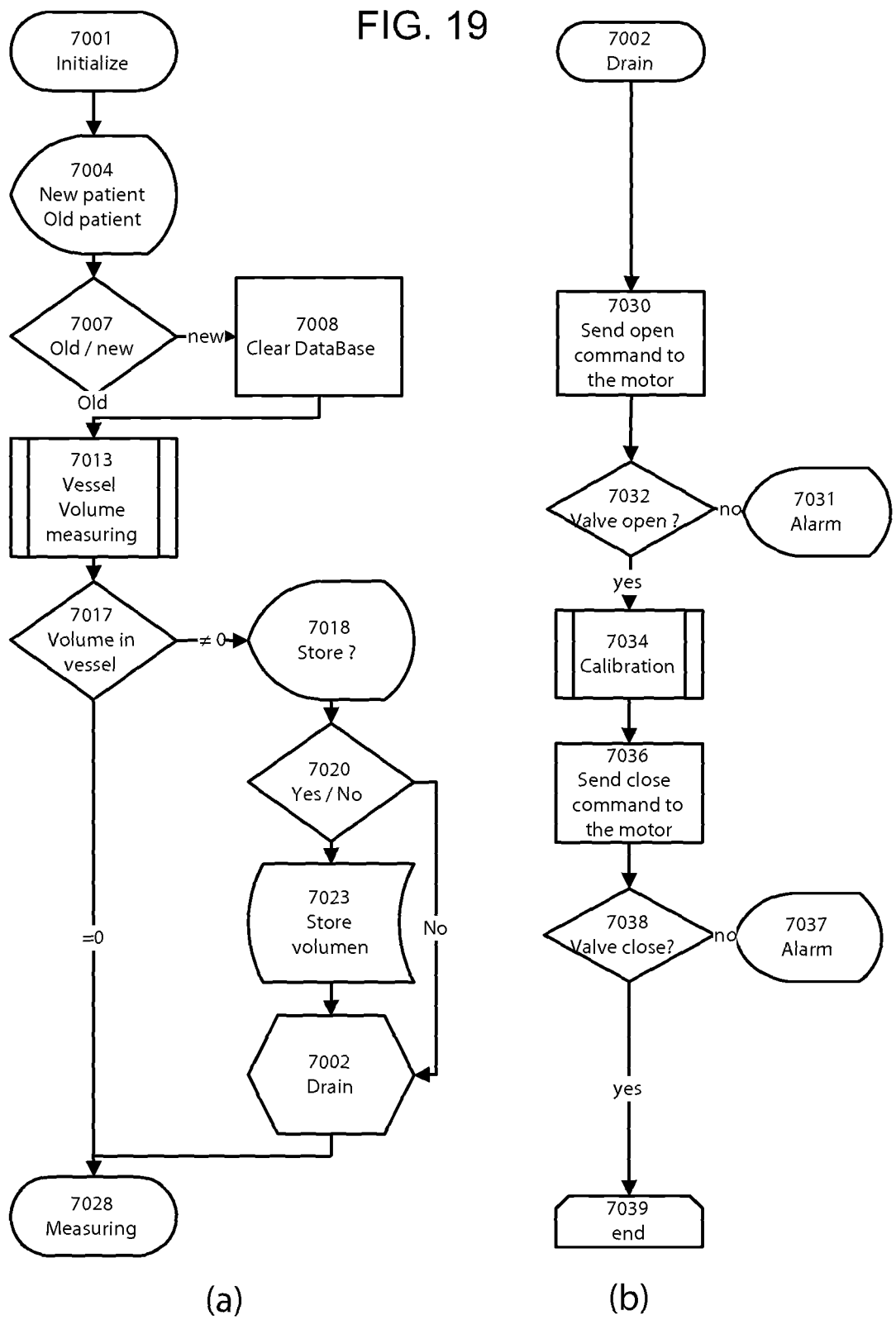
FIG. 19 is a flow chart illustrating initiation and drain routines.

FIG. 19(*a*) depicts the system flow chart for the initialization routine 7001, which initializes the system on power on. Thereafter routine 7004 waits for user input as to the patient identity 7007 whether it be old or new, which in the first case (old) will continue from previous point and in the second case (new) the system will clear the data base 7008. Vessel volume measuring 7013 will check the absence or presence of liquid in the vessel, 7017 in which case if null the measuring subroutine 7028 is activated and if not then a display routine 7018 "The vessel is not empty, store current volume?" is activated and system waits for user input 7020, if 'No' then system skips to subroutine 7002 and drains the vessel. If 'Yes' the system stores the volume 7023 and continues to the Drain subroutine 7002 and drains the vessel. After Drain 7002 the system activates the measuring subroutine 7028.

FIG. 19(*b*) Upon activation of subroutine 7002 a command to open motor 7030 is sent, system checks if the valve has opened 7032, if 'no' then an alarm is activated 7031, if 'yes' then the calibration subroutine 7034 is activated. Upon completion of the calibration subroutine 7034 a command is sent to motor 7036 to close valve. System checks if valve was closed 7038 if 'no' then the alarm 7037 is activated, if 'yes' then the system ends current subroutine 7002 by activating end block 7039. After end 7039 the system resumes the parent routine.

Figure 20:
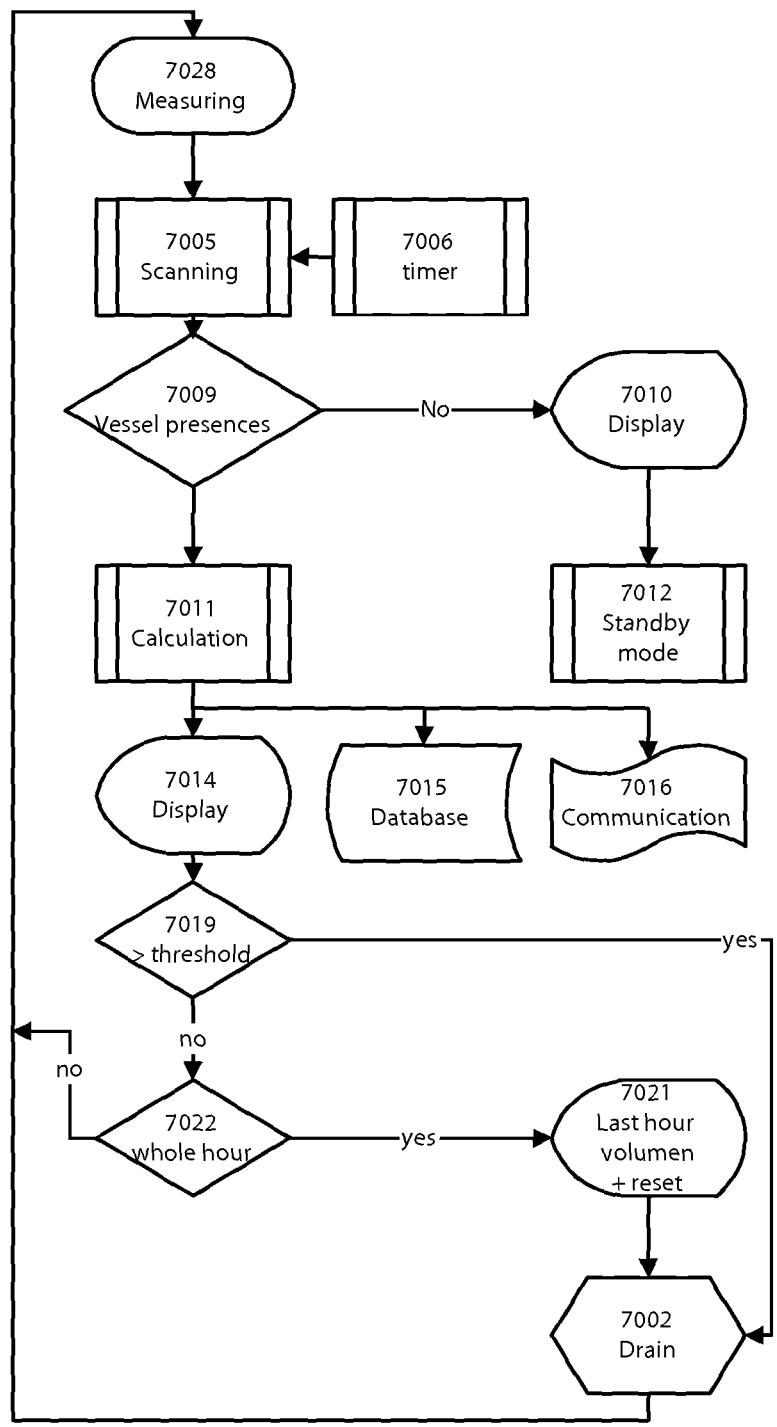
FIG. 20 is a flow chart illustrating the measuring routine.

FIG. 20 depicts the flow chart for the measuring subroutine 7028 that scans for a vessel 7005 every clock tick predefined by timer 7006. Vessel presence 7009 is checked, if 'no' activates the display 7010, "insert vessel" which initiates standby mode 7012 until placement of vessel. If 'yes' calculates 7011 the volume of liquid and updates the display 7014, database 7015 and sends data via communication 7016. System compares the volume 7019, if larger then threshold value (e.g. 100 CC) the system initiates Drain subroutine 7002, if smaller then threshold value then the system checks if a whole hour has past 7022, if 'no' then system continues to beginning of measuring subroutine 7028, If 'yes' then the system updates the previous hour display and measured volume, and zeroes the current hour display 7021. Subsequently the system will initiate the Drain subroutine 7002 and returns to head of subroutine 7028.

Figure 21:
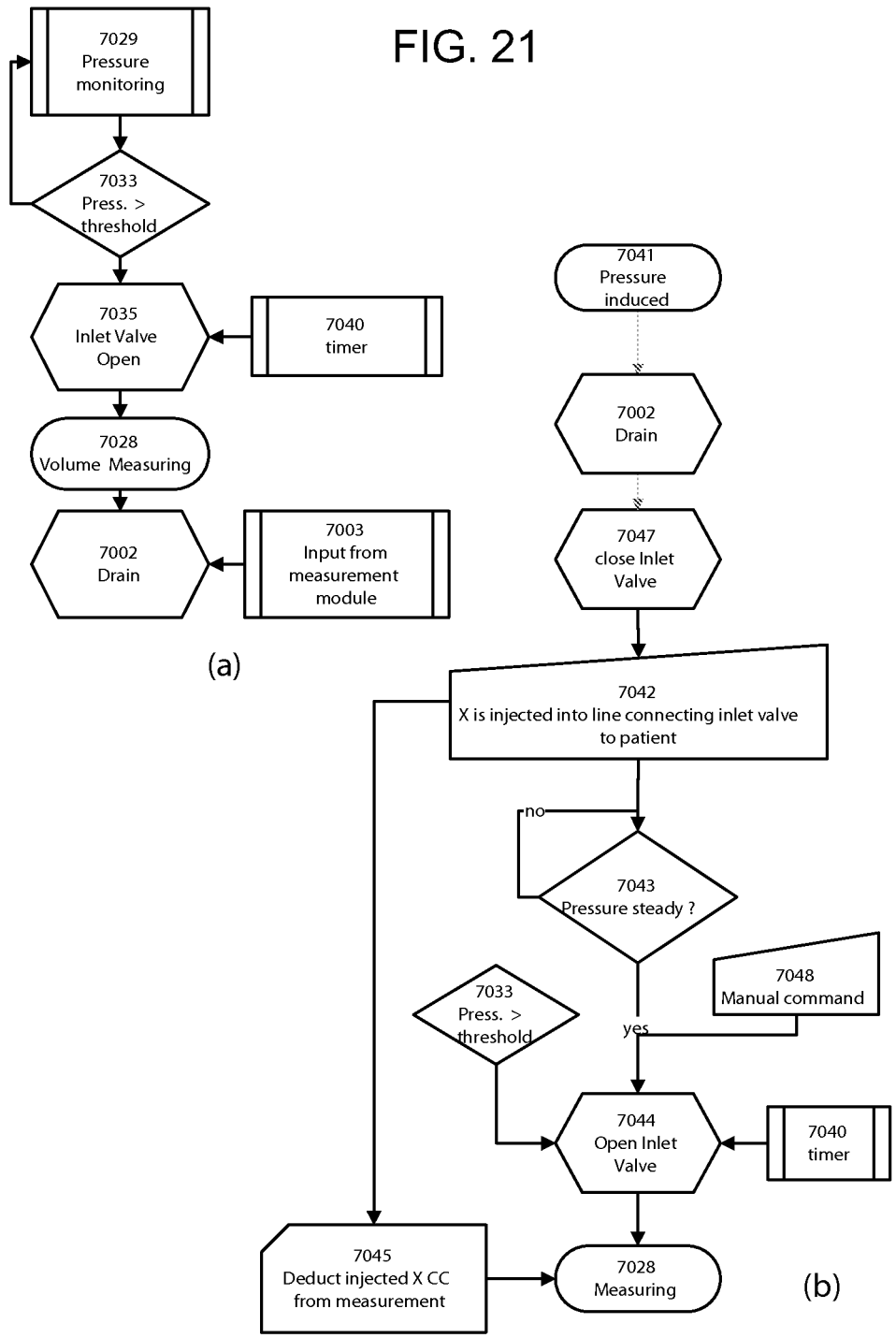
FIG. 21 is a flow chart illustrating routines relevant to a double valve system including monitoring pressure threshold and pressure routines.

FIG. 21 depicts pressure threshold and induced pressure routines relevant to double valve systems. FIG. 21(*a*) depicts the pressure monitoring 7029 routine wherein the monitored pressure is compared to threshold 7033. This process is looped as long as pressure is lower than threshold. If pressure exceeds threshold or timer trigger 7040 is induced then the inlet valve is open 7035. Subsequently volume is measured 7028 and the system is drained 7002. During pressure measuring routine 7029 the Drain subroutine 7002 can also be activated by measurement module 7003 according to settings defined in measurement module 7003. FIG. 21(*b*) concerns the pressure induced Routine 7041 and is activated when pressure is induced by manually injection of saline into the patient via the drain line connected to the inlet valve. Upon initiation the drain subroutine 7002 is activated and when finished the inlet valve is closed 7047. A predefined amount 'X' of Saline is injected into line connecting inlet valve and patient 7042. The inlet valve is opened 7044 upon any one of the following triggers: pressure reaches steady value 7043; pressure crosses threshold 7033, timer opening 7040 and manual command 7048. Any combination of said triggers can be used and is predefined in software definitions. After the opening of inlet valve 7044 the measuring subroutine 7028 is activated with a deduction of the 'X' volume of Saline injected 7045.

Summarizing the foregoing, the Fluid Secretion Pressure Monitor (FSPM) unit includes as its main components a disposable molded plastic collecting vessel and a reusable electronic unit. The collecting vessel has a cover provided with an inlet that includes a port or connector and may include a venting filter and a sampling port. The collecting vessel may be configured with an upper enlarged portion the top part of which is rectangular in cross section with knobs projecting on opposite sides for hanging the vessel on a bed; an intermediate portion and a lower portion constituting the rest of the vessel. The vessel may have a hexagonal part with a rear part trapezoidal in cross section with the smaller base of the trapezoid at the rear and serving as the optical portion. The front face of each of the portions of the collecting vessel can be marked with indicia to indicate a collected fluids measuring scale. Wall sections define inclined under shoulders for mounting on the electronic unit. The container may have a bifurcated hanger support for hanging secondary reservoirs.

The secondary reservoir has an inlet port that engages with lower outlet connector of the collecting vessel. An outlet valve operable manually or automatically by an electro-mechanism controls the outlet of the collecting vessel. For urine a high flow tube is used. For CSF a low flow tube is used. The vessel also contains an overflow arrangement as a security measure.

Also, a double motor, double valved FSPM unit can be provided and it can be connected to a disposable pressure transducer (DPT) fixed at the level of the organ being drained via a tube and a stopcock provided with a control knob.

Further relative to the optical portion of the vessel there is juxtaposed an optical segment that consists of clamping brackets, the vessel type identifiers, the light emitting diodes (LEDs) and the photodetector strip to effect measurements responsive to the controls imposed by the electronic unit. Also, special provision is made for mounting of the apparatus bedside in a horizontal manner. A drainage tube leads from a catheter inserted into a body cavity, e.g., the patient's bladder, and is connected to the inlet of the apparatus that leads to the collection vessel. If a double motor FSPM unit is being used an upper inlet valve is present and a pole or rod is attached to the bed frame or a free stand is provided on which is slidingly mounted a pressure transducer and a height beam indicator that can be adjusted or controlled to the level of the patient's drained cavity. A second tube leads from the drained cavity or is taken off the drainage tube and is operatively connected to a pressure transducer. Both the transducer and height beam indicator output electrical signals indicative of the values sensed and transmit these signals to the electronic unit. Also a remote unit can be electrically coupled to the FSPM unit via an operative cable.

Liquid level is measured in the vessel by an optical segment that consists of a vertical array of LEDs coacting with a vertically oriented photodetector strip. The LEDs are powered and controlled by a microprocessor computing unit according to software programs, as explained above.

A rechargeable battery can be included as the power source for all components of the FSPM unit. The rechargeable battery can be recharged through the USB port of the FSPM unit when connected to a computer, or through an AC power adapter connected to an external power source.

The measuring of the liquid's surface height $h_m$ is accomplished by scanning the space of the optical segment of the optical portion of the transparent measuring vessel. This scanning is based on the refraction of the emitters' rays on the boundary of two media due to the special measuring vessel's construction. Various vessel configurations can be used. A novel identification device and technique is included for automatically determining the type of vessel connected to the electronic unit that uses the two upper emitters for vessel type identifiers using opaque tabs. Special programs have been described for the operation of the FSPM unit automatically in several modes.

In addition to the foregoing, the invention relates to a computer readable media that has recorded program instructions for carrying out the software programs shown in the flowcharts of FIGS. 19-21 and by means of the apparatus illustrated in FIGS. 13 and 14.

The above description sets forth preferred embodiments of the present invention. Various modifications and changes to the preferred embodiments will be apparent to those of ordinary skill in the art without departing from the teachings, spirit and scope of the present invention. Such modifications and changes are deemed to come within the scope of the appended claims.

What is claimed:

1. Non-transitory computer readable media having recorded thereon program instructions for controlling a bedside apparatus to collect and measure body liquid issuing from a patient, the bedside apparatus composed of a holder for holding a collecting and measuring rigid vessel in a horizontal orientation, said holder defining a vertically oriented optical segment having opposite sides, a vertical array of spaced LEDs mounted in the holder on one said opposite side of said optical segment, a single vertically oriented photodetector device having an output mounted in said holder on the other opposite side of said optical segment to receive light from said vertical array of spaced LEDs, the light from each said LED overlapping adjacent vertically spaced LEDs, wherein the disposable collecting and measuring rigid vessel having an inlet and a configuration whereby a portion of the vessel fits in said optical segment for light to pass therethrough and wherein the inlet can be connected to a catheter outputting liquid from a patient in order to collect liquid in the vessel;

a disposable rigid collecting and measuring vessel of a preselected set of types having an inlet at its top connectable via an inlet valve to a catheter outputting liquid from a patient and an outlet at its bottom and defining a transparent optical part extending vertically from bottom to top of said measuring vessel that is geometrically configured such that light as it passes through the optical part of the measuring vessel has a predetermined refraction in dependence on whether there is liquid present in the light path, which predetermined refraction causes said light to by-pass the photodetector device;

said apparatus including an identifier capable of differentiating between different types of measuring vessels;

said program instructions including instructions operative (a) for serially and cyclically at defined intervals scanning the LEDs in succession to detect the intensity or luminance of light from each LED detected by the single vertically oriented photodetector device and to output signals correlated to the detected intensity or luminance for each LED, (b) for storing said output signals in memory, (c) for processing said output signals according to the predetermined algorithm to determine the height of collected liquid in the optical part of the measuring vessel, and (d) for storing information about the height of collected liquid in memory;

said program instructions including further instructions for operatively determining via a microprocessor and a preselected algorithm based on the output of the single vertically oriented photodetector device of the level of liquid in said optical segment (e) for calculating and outputting an indication of the volume of liquid in said measuring vessel; (f) for actuating a valve controller for opening an outlet valve in response to a signal generated by a sensed condition of the liquid volume in the measuring vessel for draining liquid contained in said vessel; and (q) for outputting the calculated value of liquid volume contained in said vessel at the time of the sensed condition and storing same in memory;

wherein the program instruction include still further instructions for carrying out multiple scans for each defined interval scanning with recording of results in a temporary memory; analysis of temporary recorded results and correction by removal of artifacts; averaging of corrected temporary recorded results; and storing of the remaining averaged results for data processing to control draining of liquid from said vessel according to a sensed condition of one of (i) predetermined time intervals and (ii) predetermined fluid level thus enabling clinical staff to view the measuring vessel with respect to collected liquid characteristics including color, blood in the fluid and sedimentation.

2. Computer readable media according to claim 1 including further program instructions for displaying the calculated value of liquid contained in said vessel.

3. Computer readable media according to claim 1 wherein the sensed condition is one of volume and time.

4. Computer readable media according to claim 1 further including program instructions for monitoring pressure in the body cavity, and outputting a signal indicative of the monitored pressure.

5. Computer readable media according to claim 1 further including program instructions for controlling the inlet to the vessel responsive to the pressure in the body cavity.

6. A bedside apparatus to collect and monitor liquids output from a catheterized patient comprising: a holder mountable in a horizontal orientation defining a vertically oriented optical segment cavity having opposite sides, a vertically array of spaced LEDs mounted along a height of said optical segment cavity on one side of said optical segment cavity with their optical axes in parallel substantially perpendicular to the height of said optical segment cavity with the LEDs equally space vertically and each directing its diverging light ray toward the other side of said optical segment cavity, said LEDs being configured so that every LED's diverging light ray partially overlaps the light rays of its upper and lower neighboring LEDs as it traverses the optical segment cavity, and a single vertically oriented photodetector device mounted in said holder on the opposite side of said optical segment cavity, the photodetector device positioned to receive non-refracted light from each LED of said vertical array of spaced LEDs that passes through the optical segment cavity and to output signals correlated to detected intensity or luminance;

a disposable rigid collecting and measuring vessel of a preselected set of types having an inlet at its top connectable via an inlet valve to a catheter outputting liquid from a patient and an outlet at its bottom and defining a transparent optical part extending vertically from bottom to top of said measuring vessel that is geometrically configured such that light as it passes through the optical part of the measuring vessel has a predetermined refraction in dependence on whether there is liquid present in the light path, which predetermined refraction causes said light to by-pass the photodetector device;

said apparatus including an identifier capable of differentiating between different types of measuring vessels;

said measuring vessel being demountably held on said holder in a fixed position with its optical part positioned vertically in said vertically oriented optical segment cavity so that light from said vertically spaced LEDs is directed through the optical part of said measuring vessel as it traverses said optical segment cavity, with the single vertically oriented photodetector device receiving only unrefracted light;

said holder further includes (i) a memory and (ii) a microprocessor including a program operative (a) for serially and cyclically at defined intervals scanning the LEDs in succession to detect the intensity or luminance of light from each LED detected by the vertically oriented photodetector device and to output signals correlated to the detected intensity or luminance for each LED, (b) for storing said output signals in said memory, (c) for processing said output signals according to a predetermined algorithm to determine the height of collected liquid in the optical part of the measuring vessel, and (d) for storing information about the height of collected liquid in memory, wherein the program is further operative for carrying out multiple scans for each defined interval scanning with recording of results in a temporary memory; analysis of temporary recorded results and correction by removal of artifacts; averaging of corrected temporary recorded results; and storing of the remaining averaged results for data processing to determine the corrected height of collected liquid in the optical part of the measuring vessel;

said apparatus further includes at least one electrical motor having an output drive shaft that operatively engages with an outlet valve mounted on said measuring vessel, wherein operation of the at least one electric motor opens or closes the outlet valve in response to predetermined conditions of operation of the microcontroller thereby controlling draining of liquid from said vessel according to one of (i) predetermined time intervals and (ii) predetermined fluid level thus enabling clinical staff to view collected liquid characteristics including color, blood in the fluid and sedimentation.

7. Bedside apparatus according to claim 6 wherein the holder further includes at least two fixation clamps to fixate, mount and hold said measuring vessel in said fixed relationship.

8. Bedside apparatus according to claim 6 further comprising a pressure monitoring device for monitoring pressure in a draining organ of a catheterized patient and for providing an output signal indicative of the monitored pressure communicated to the microcontroller, and said microcontroller configured for controlling said inlet valve responsive to the received output signal indicative of the monitored pressure.

9. Bedside apparatus according to claim 6 wherein the apparatus further includes a hanging device to hold the apparatus horizontally.

10. The bedside apparatus according to claim 6 further including a tilt sensor for sensing angle from the horizontal of the measuring vessel and for providing an output coupled to the microprocessor to correct for any tilt of the measuring vessel from horizontal.

11. The bedside apparatus according to claim 6 further including a disposable flexible collecting bag having an inlet that is mounted on the measuring vessel with the inlet of the collecting bag coupled to the outlet of the measuring vessel so that liquid content of the measuring vessel can be periodically emptied on the basis of one of time or volume.

12. A method of monitoring a bedside apparatus to collect liquids output from a catheterized patient comprising the steps of: providing a holder mountable in a horizontal orientation defining a vertically oriented optical segment cavity having opposite sides, a vertically array of spaced LEDs mounted along a height of said optical segment cavity on one side of said optical segment cavity with their optical axes in parallel substantially perpendicular to the height of said optical segment cavity with the LEDs equally space vertically and each directing its diverging light ray toward the other side of said optical segment cavity, said LEDs being configured so that every LED's diverging light ray partially overlaps the light rays of its upper and lower neighboring LEDs as it traverses the optical segment cavity, and a single vertically oriented photodetector device mounted in said holder on the opposite side of said optical segment cavity, the photodetector device positioned to receive non-refracted light from each LED of said vertical array of spaced LEDs that passes through the optical segment cavity and outputs signals correlated to detected intensity or luminance;

providing a disposable rigid collecting and measuring vessel of a preselected set of types having an inlet at its top connectable to a catheter outputting liquid from a patient and an outlet at its bottom and defining a transparent optical part extending vertically from bottom to top of said measuring vessel that is configured such that light as it passes through the optical part of the measuring vessel has a predetermined refraction in dependence on whether there is liquid present in the light path;

differentiating between different types of measuring vessels using an identifier;

mounting said measuring vessel on said holder in a fixed position with its optical part positioned in said vertically oriented optical segment cavity so that light from said vertically spaced LEDs is directed through the optical part of said measuring vessel as it traverses said optical segment cavity, with the single vertically oriented photodetector device receiving only light that has not been refracted due to liquid in the light path;

wherein said holder further includes (i) a memory including a program and (ii) a microprocessor responsive to said non-transitory program operative (a) for serially and cyclically at defined intervals scanning the LEDs in succession to detect the intensity or luminance of light from each LED detected by the single vertically oriented photodetector device and to output signals correlated to the detected intensity or luminance for each LED, (b) for storing said output signals in said memory, (c) for processing said output signals according to a predetermined algorithm to determine the height of collected liquid in the optical part of the measuring vessel, and (d) for storing information about the height of collected liquid in memory, wherein the program is further operative for instructing the microprocessor for carrying out multiple scans for each defined interval scanning with recording of results in a temporary memory; analysis of temporary recorded results and correction by removal of artifacts; averaging of corrected temporary recorded results and storing of the remaining averaged results for data processing to determine the corrected height of collected liquid in the optical part of the measuring vessel;

providing further at least one electrical motor having an output drive shaft that operatively engages with an outlet valve mounted on said measuring vessel, wherein operation of the at least one electric motor opens or closes the outlet valve in response to predetermined conditions of operation of the microcontroller thereby controlling draining of liquid from said vessel according to one of (i) predetermined time intervals and (ii) predetermined fluid level thus enabling clinical staff to view collected liquid characteristics including color, blood in the fluid and sedimentation;

scanning the LEDs cyclically at successive defined intervals to detect the intensity or luminance of light of each LED by the single vertically oriented photodetector device and to output signals for each defined interval correlated to the detected intensity or luminance of each LED;

storing said output signals in memory; carrying out multiple scans for each defined interval scanning with recording of results in a temporary memory; processing said output signals for each defined interval according to a predetermined algorithm that a. analyzes temporary recorded results and correcting by removal of artifacts; b. averages corrected temporary recorded results; c. stores the remaining averaged results; and d. then data processes the averaged results to determine the corrected height of collected liquid in the optical part of the measuring vessel at each defined interval; and storing in memory information related to volume of liquid contained in the measuring vessel based on the determined height of collected liquid for each defined interval.

13. Method according to claim 12 further including the step of controlling said inlet.

14. Method according to claim 12 including the further step of optically identifying the type of disposable measuring vessel.

15. Method according to claim 12 including the further step of the operatively controlling an electrical motor having an output drive shaft that operatively engages with a valve in the inlet, and micro-controlling operatively a level sensing device and the electric motor to open or close the valve in response to predetermined conditions.

16. Method according to claim 12 including the further steps of operatively controlling an output valve to control draining of liquid from said vessel according to one of predetermined time intervals and predetermined fluid level of liquid collected in said measuring vessel thus enabling clinical staff to view collected liquid characteristics including color, blood in the fluid and sedimentation.

17. Method according to claim 12 comprising the further step of monitoring pressure in a draining organ of a catheterized patient; providing an output signal indicative of the monitored pressure; and controlling the disposable collecting vessel responsive to the output signal indicative of the monitored pressure.

18. Method according to claim 12 including the further steps of inducing pressure by administrating fluid into the draining organ, and adjusting the volume of liquid output by subtracting the additional fluid administrated to induce pressure.

19. Method according to claim 12 including the step of opening the outlet of the measuring vessel in response to receiving a signal indicative of a predetermined volume in said measuring vessel.

20. Method according to claim 12 including the step of opening the outlet of the measuring vessel in response to receiving a signal indicative of a predetermined time.

21. Method according to claim 12 including the further step of hanging the defined vessel horizontally from a bed in which a patient is lying and from whom fluid is being drained.

22. Method according to claim 12 including the further steps of monitoring the vessel for a tilt, outputting a tilt signal responsive to the tilt condition of the vessel, and determining responsive to the tilt output signal the relative horizontal orientation of the vessel.

23. Method according to claim 12 including the further steps of monitoring the measuring vessel for overflowing fluid that rises above a predetermined threshold, and responsive thereto draining the overflowing fluid through a bypass channel provided in an outlet valve.

24. The method according to claim 12 including the further step of one of (i) displaying visually the determined volume of liquid updated for each defined interval, and (ii) transmitting data periodically via a communication port.

* * * * *